(12) United States Patent
Nordt, III

(10) Patent No.: US 12,127,772 B2
(45) Date of Patent: *Oct. 29, 2024

(54) BONE PLATE APPARATUS WITH ARTICULATING JOINTS

(71) Applicant: William E. Nordt, III, Charles City, VA (US)

(72) Inventor: William E. Nordt, III, Charles City, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/241,946

(22) Filed: Sep. 4, 2023

(65) Prior Publication Data

US 2024/0050135 A1    Feb. 15, 2024

Related U.S. Application Data

(63) Continuation of application No. 17/666,422, filed on Feb. 7, 2022, now Pat. No. 11,744,621, which is a continuation of application No. 16/522,847, filed on Jul. 26, 2019, now Pat. No. 11,241,263, which is a continuation-in-part of application No. 16/294,239, filed on Mar. 6, 2019, now abandoned.

(60) Provisional application No. 62/639,465, filed on Mar. 6, 2018.

(51) Int. Cl.
| | |
|---|---|
| *A61B 17/80* | (2006.01) |
| *A61B 17/00* | (2006.01) |
| *A61B 17/56* | (2006.01) |
| *A61B 17/84* | (2006.01) |
| *A61B 17/86* | (2006.01) |

(52) U.S. Cl.
CPC .... *A61B 17/80* (2013.01); *A61B 2017/00004* (2013.01); *A61B 2017/0011* (2013.01); *A61B 2017/00398* (2013.01); *A61B 2017/00862* (2013.01); *A61B 2017/0092* (2013.01); *A61B 2017/564* (2013.01); *A61B 17/842* (2013.01); *A61B 17/86* (2013.01)

(58) Field of Classification Search
CPC ....... A61B 17/80; A61B 17/842; A61B 17/86; A61B 2017/00004; A61B 2017/0011; A61B 2017/00398; A61B 2017/0092; A61B 2017/564
See application file for complete search history.

(56) References Cited

U.S. PATENT DOCUMENTS

| | | | |
|---|---|---|---|
| 10,258,377 B1 * | 4/2019 | Lavi | A61B 34/10 |
| 2007/0250172 A1 * | 10/2007 | Moskowitz | A61B 17/68 623/17.15 |
| 2016/0113681 A1 * | 4/2016 | Singh | A61B 17/8875 606/104 |
| 2017/0277859 A1 * | 9/2017 | Burgherr | G16H 50/50 |

* cited by examiner

*Primary Examiner* — Kevin T Truong
*Assistant Examiner* — Diana Jones
(74) *Attorney, Agent, or Firm* — TILLMAN WRIGHT, PLLC; Chad D. Tillman; James D. Wright

(57) ABSTRACT

A bone plate apparatus comprises a first plate comprising one or more openings configured for use in securing the first plate to a portion of a bone, a second plate comprising one or more openings configured for use in securing the second plate to a portion of a bone, and a linking segment. The first plate is connected to the linking segment at a first articulating joint, and the second plate is connected to the linking segment at a second articulating joint.

20 Claims, 41 Drawing Sheets

BONE PLATE APPARATUS WITH ARTICULATING JOINTS

CROSS-REFERENCE TO RELATED APPLICATION

The present application is a continuation of, and claims priority under 35 U.S.C. § 120 to, U.S. nonprovisional patent application Ser. No. 17/666,422, filed Feb. 7, 2022, now U.S. Pat. No. 11,744,621, which '422 application and '621 patent are incorporated herein by reference, and which '422 application is a continuation of, and claims priority under § 120 to U.S. nonprovisional patent application Ser. No. 16/522,847, filed Jul. 26, 2019, now U.S. Pat. No. 11,241,263, which '847 application and '263 patent are incorporated herein by reference, and which '847 application is a U.S. continuation-in-part patent application of, and claims priority under 35 U.S.C. § 120 to, U.S. nonprovisional patent application Ser. No. 16/294,239, filed Mar. 6, 2019, which '239 application and any patent application publication thereof are incorporated by reference herein, and which '239 application is a U.S. nonprovisional patent application of, and claims priority under 35 U.S.C. § 119 (e) to, U.S. provisional patent application 62/639,465, filed Mar. 6, 2018, which provisional patent application is incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to bone plates, e.g. bone plates for securement to a bone of a patient during a surgical procedure.

Although adjustable bone plates are known, including adjustable bone plates with joints providing a connection between plate members such as disclosed in U.S. Pat. No. 7,704,251, needs exist for improvements related to bone plates. These needs and other needs are addressed by one or more aspects of the present invention.

SUMMARY OF THE INVENTION

The present invention includes many aspects and features. Moreover, while many aspects and features relate to, and are described in, the context of adjustable bone plates, the present invention is not limited to use only in this context, as will become apparent from the following summaries and detailed descriptions of aspects, features, and one or more embodiments of the present invention.

Accordingly, one aspect of the present invention relates to a bone plate apparatus comprising a first plate comprising one or more openings configured for use in securing the first plate to a portion of a bone; a second plate comprising one or more openings configured for use in securing the second plate to a portion of a bone; and a linking segment. The first plate is connected to the linking segment at a first articulating joint, and the second plate is connected to the linking segment at a second articulating joint.

In a feature of this aspect, the first articulating joint is configured for movement in two dimensions.

In a feature of this aspect, the first articulating joint is configured for movement in three dimensions.

In a feature of this aspect, the first articulating joint is configured for free movement in three dimensions.

In a feature of this aspect, the first articulating joint is configured for free simultaneous movement through two perpendicular planes.

In a feature of this aspect, the first articulating joint is configured to allow for rotation of the first plate and linking segment relative to one another.

In a feature of this aspect, the first articulating joint is configured to restrict motion to a particular range of motion.

In a feature of this aspect, the first articulating joint is configured for free, multi-dimensional movement simultaneously through two perpendicular planes, but with a limited range of motion.

In a feature of this aspect, the first articulating joint is a ball and socket joint.

In a feature of this aspect, the first articulating joint is a ball and socket joint with range of motion limited by the shape of the socket.

In a feature of this aspect, a length of the linking segment is adjustable.

In a feature of this aspect, a length of the linking segment is adjustable, and the linking segment comprises an inner segment partially received within an outer segment.

In a feature of this aspect, a length of the linking segment is adjustable, the linking segment comprises an inner segment partially received within an outer segment, and the inner and outer segments of the linking segment are adjustably mated together with threading such that the length of the linking segment may be adjusted via rotation of the inner and outer segments relative to one another.

In a feature of this aspect, a length of the linking segment is adjustable, and the bone plate apparatus includes a locking mechanism to lock adjustability of the length of the linking segment.

In a feature of this aspect, the linking segment is removably connected to the first plate.

In a feature of this aspect, the linking segment is removably connected to the second plate.

In a feature of this aspect, the bone plate apparatus comprises a first locking mechanism for locking adjustment at the first articulating joint.

In a feature of this aspect, the first articulating joint comprises one or more curved surfaces.

In a feature of this aspect, the first articulating joint comprises one or more curved concave surfaces and one or more curved convex surfaces, with the curved concave surfaces being configured to mate in adjustable engagement with the curved convex surfaces.

In a feature of this aspect, the first articulating joint comprises one or more channels enabling rotative movement.

In a feature of this aspect, the bone plate apparatus comprises one or more orientation adjustment pins.

In a feature of this aspect, the linking segment is rigid.

In a feature of this aspect, the linking segment is semi-rigid.

In a feature of this aspect, one or more of the first plate, the second plate, and the linking segment are rigid.

In a feature of this aspect, one or more of the first plate, the second plate, and the linking segment are semi-rigid.

In a feature of this aspect, one or more of the first plate, the second plate, and the linking segment are radiolucent.

In a feature of this aspect, one or more of the first plate, the second plate, and the linking segment are compressible.

In a feature of this aspect, one or more of the first plate, the second plate, and the linking segment are distractable.

In a feature of this aspect, one or more of the first plate, the second plate, and the linking segment are bendable or flexible.

In a feature of this aspect, one or more of the first plate, the second plate, and the linking segment are absorbable.

In a feature of this aspect, one or more of the first plate, the second plate, and the linking segment are dissolvable.

In a feature of this aspect, the bone plate apparatus is mechanized.

In a feature of this aspect, the bone plate apparatus comprises one or more servo-motors.

In a feature of this aspect, one or more of the first plate, the second plate, and the linking segment are rigid.

In a feature of this aspect, the bone plate apparatus comprises synthetic material.

In a feature of this aspect, the bone plate apparatus biological material.

In a feature of this aspect, the bone plate apparatus comprises metal.

In a feature of this aspect, the bone plate apparatus comprises material for stimulating healing.

In a feature of this aspect, the bone plate apparatus comprises a sensor.

In a feature of this aspect, the bone plate apparatus comprises a strain gauge.

In a feature of this aspect, the bone plate apparatus comprises a shock absorber that functions as a strain gauge.

In a feature of this aspect, a component of a bone plate apparatus comprises a piezoelectric material.

In a feature of this aspect, a component of a bone plate apparatus comprises a piezoelectric sensor.

In a feature of this aspect, a component of a bone plate apparatus comprises a piezoelectric sensor which utilizes the piezoelectric effect to measure changes in strain or force by converting them to electric charge which is then measured by a sensor.

In a feature of this aspect, a component of a bone plate apparatus comprises an integrated circuit piezoelectric sensor.

In a feature of this aspect, a component of a bone plate apparatus comprises a piezoelectric accelerometer.

In a feature of this aspect, a component of a bone plate apparatus comprises a flex sensor, a gyroscopic sensor, an impact sensor, an inclinometer, a position sensor, an angular rate sensor, a shock detector, a tilt sensor, a load cell, or a force gauge or sensor.

In a feature of this aspect, a sensor is embedded in or secured to a plate or linking segment. In a feature of this aspect, a segment of a plate or linking segment has sensor capabilities.

In a feature of this aspect, the bone plate apparatus comprises a secondary support adjacent to the linking segment.

In a feature of this aspect, the first plate comprises a flat surface configured to engage a bone portion.

In a feature of this aspect, the first plate comprises a curved surface configured to engage a bone portion.

In a feature of this aspect, the one or more openings of the first plate comprise one or more openings configured for receipt of a bone screw.

In a feature of this aspect, the bone plate apparatus is secured to bone portions by a plurality of bone screws.

In a feature of this aspect, the bone plate apparatus is secured to bone portions by a cable.

Another aspect relates to a method comprising providing a bone plate apparatus including a first plate comprising one or more openings configured for use in securing the first plate to a portion of a bone; a second plate comprising one or more openings configured for use in securing the second plate to a portion of a bone; and a linking segment. The first plate is connected to the linking segment at a first articulating joint. The second plate is connected to the linking segment at a second articulating joint. The method further comprises attaching the first plate to bone at a first bone location; attaching the second plate to bone at a second bone location; orienting the first plate relative to the second plate by manipulating the bone plate apparatus including effecting adjustment at one of the articulating joints; and locking the first and second articulating joints.

Another aspect relates to a method comprising providing a bone plate apparatus including a first plate comprising one or more openings configured for use in securing the first plate to a portion of a bone; a second plate comprising one or more openings configured for use in securing the second plate to a portion of a bone; and a linking segment. The first plate is connected to the linking segment at a first articulating joint. The second plate is connected to the linking segment at a second articulating joint. The method further comprises attaching the first plate to bone at a first bone location; attaching the second plate to bone at a second bone location; connecting the linking segment to the first plate; connecting the linking segment to the second plate; and locking the first and second articulating joints.

Another aspect relates to a method comprising providing a bone plate apparatus including a first plate comprising one or more openings configured for use in securing the first plate to a portion of a bone; a second plate comprising one or more openings configured for use in securing the second plate to a portion of a bone; and a linking segment. The first plate is connected to the linking segment at a first articulating joint. The second plate is connected to the linking segment at a second articulating joint. The method further comprises attaching the first plate to bone at a first bone location; connecting the linking segment to the first plate; connecting the linking segment to the second plate; orienting the first plate relative to the second plate by manipulating the bone plate apparatus including effecting adjustment at one of the articulating joints; attaching the second plate to bone at a second bone location; and locking the first and second articulating joints.

In a feature of one or more aspects, a method further comprises unlocking one or more of the articulating joints; orienting the first plate relative to the second plate by manipulating the bone plate apparatus including effecting adjustment at one of the articulating joints; and locking the first and second articulating joints.

In a feature of one or more aspects, a method further comprises effecting x-ray imaging of the installed bone plate apparatus; unlocking one or more of the articulating joints; orienting, based on x-ray imaging information, the first plate relative to the second plate by manipulating the bone plate apparatus including effecting adjustment at one of the articulating joints; and locking the first and second articulating joints.

Another aspect relates to a method comprising providing a bone plate apparatus including a first plate comprising one or more openings configured for use in securing the first plate to a portion of a bone; a second plate comprising one or more openings configured for use in securing the second plate to a portion of a bone; a linking segment; a sensor configured to generate digital sensor data; and a wireless communication component. The first plate is connected to the linking segment at a first articulating joint, and the second plate is connected to the linking segment at a second articulating joint. The method further includes attaching the first plate to bone at a first bone location; attaching the second plate to bone at a second bone location; orienting the first plate relative to the second plate by manipulating the bone plate apparatus including effecting adjustment at one of the articulating joints; locking the first and second articulating joints; and communicating, by the wireless communication component of the bone plate apparatus, sensor data from the sensor of the bone plate apparatus.

Another aspect relates to a bone plate apparatus including a first plate comprising one or more openings configured for use in securing the first plate to a portion of a bone; a second plate comprising one or more openings configured for use in securing the second plate to a portion of a bone; and a linking segment. The first plate is connected to the linking segment at a first articulating joint. The second plate is connected to the linking segment at a second articulating joint. Each of the articulating joints is a liquid multi-directional joint comprising a bi-phasic material interface.

In addition to the aforementioned aspects and features of the present invention, it should be noted that the present invention further encompasses the various logical combinations and subcombinations of such aspects and features. Thus, for example, claims in this or a divisional or continuing patent application or applications may be separately directed to any aspect, feature, or embodiment disclosed herein, or combination thereof, without requiring any other aspect, feature, or embodiment.

BRIEF DESCRIPTION OF THE DRAWINGS

One or more preferred embodiments of the present invention now will be described in detail with reference to the accompanying drawings, wherein the same elements are referred to with the same reference numerals.

DETAILED DESCRIPTION

Figure 1:
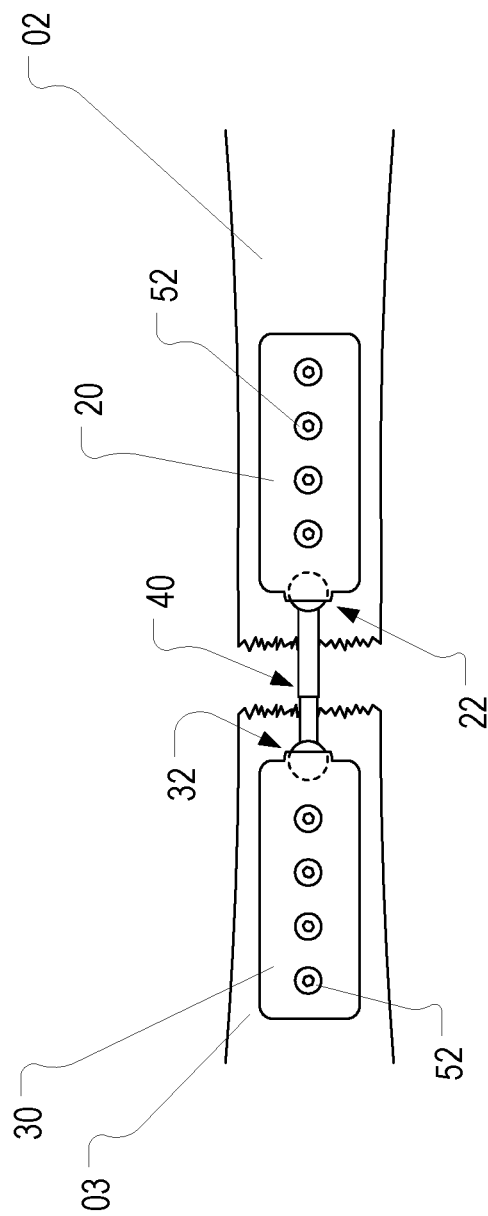
FIG. 1 provides a fanciful illustration of an articulating bone plate apparatus in accordance with one or more preferred embodiments.

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Furthermore, an embodiment of the invention may incorporate only one or a plurality of the aspects of the invention disclosed herein; only one or a plurality of the features disclosed herein; or combination thereof. As such, many embodiments are implicitly disclosed herein and fall within the scope of what is regarded as the invention.

Accordingly, while the invention is described herein in detail in relation to one or more embodiments, it is to be understood that this disclosure is illustrative and exemplary of the invention, and is made merely for the purposes of providing a full and enabling disclosure of the invention. The detailed disclosure herein of one or more embodiments is not intended, nor is to be construed, to limit the scope of patent protection afforded the invention in any claim of a patent issuing here from, which scope is to be defined by the claims and the equivalents thereof. It is not intended that the scope of patent protection afforded the invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

With regard solely to construction of any claim with respect to the United States, no claim element is to be interpreted under 35 U.S.C. 112(f) unless the explicit phrase "means for" or "step for" is actually used in such claim element, whereupon this statutory provision is intended to and should apply in the interpretation of such claim element. With regard to any method claim including a condition precedent step, such method requires the condition precedent to be met and the step to be performed at least once during performance of the claimed method.

Furthermore, it is important to note that, as used herein, "a" and "an" each generally denotes "at least one", but does not exclude a plurality unless the contextual use dictates otherwise. Thus, reference to "a picnic basket having an apple" describes "a picnic basket having at least one apple" as well as "a picnic basket having apples". In contrast, reference to "a picnic basket having a single apple" describes "a picnic basket having only one apple".

When used herein to join a list of items, "or" denotes "at least one of the items", but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers". When used herein to join a list of items, "and" denotes "all of the items of the list". Thus, reference to "a picnic basket having cheese and crackers" describes "a picnic basket having cheese, wherein the picnic basket further has crackers", as well as describes "a picnic basket having crackers, wherein the picnic basket further has cheese".

Referring now to the drawings, one or more preferred embodiments of the invention are next described. The following description of one or more preferred embodiments is merely exemplary in nature and is in no way intended to limit the invention, its implementations, or uses.

General Overview

Turning now to the drawings, FIG. 1 provides a fanciful illustration of an articulating bone plate apparatus 10 in accordance with one or more preferred embodiments. The articulating bone plate apparatus 10 includes a first plate 20, which is screwed with bone screws 52 to a bone portion 02, and a second plate 30, which is screwed with bone screws 52 to a bone portion 03. The first plate 20 and the second plate 30 are connected together by a linking segment 40. The linking segment 40 is connected to the first plate 20 at a first articulating joint 22, and is connected to the second plate 30 at a second articulating joint 32.

Figure 2:
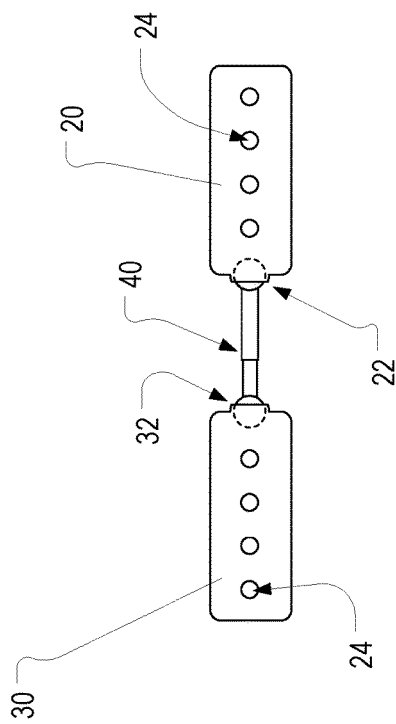
FIG. 2 illustrates the articulating bone plate apparatus of FIG. 1, illustrated not secured to bone portions.

FIG. 2 illustrates the same articulating bone plate apparatus 10 of FIG. 1, illustrated not secured to bone portions 02,03. As can be seen in FIG. 2, the first plate 20 and the second plate 30 each include screw openings 24 configured to receive a bone screw.

In accordance with various preferred implementations, an articulating joint may be configured for movement in multiple dimensions, including three dimensions (e.g. may be configured for movement through one or more planes, including movement through two perpendicular planes), and may be configured for free multi-dimensional movement (e.g. free movement simultaneously in three dimensions or through two perpendicular planes). In accordance with one or more preferred implementations, an apparatus may include multiple articulating mechanisms at an articulating joint each providing for movement through a plane, and may further allow for rotation of articulating mechanisms relative to one another. In accordance with one or more preferred implementations, an articulating joint may be configured to restrict or limit movement to a particular range of motion.

With respect to the articulating bone plate apparatus 10 illustrated in FIGS. 1-2, each articulating joint 22,32 is configured for free multi-dimensional movement, but with a restricted range of motion. In particular, each articulating joint 22,32 comprises a ball and socket joint, with range of motion limited by the shape of the socket joint.

Figure 3:
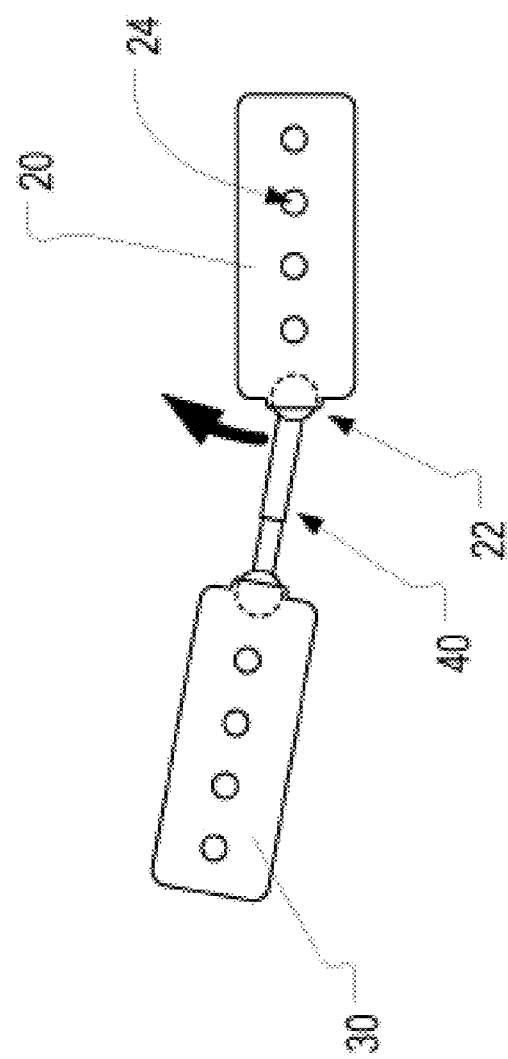
FIGS. 3-6 illustrate adjustment of the bone plate apparatus of FIG. 1.
Figure 4:
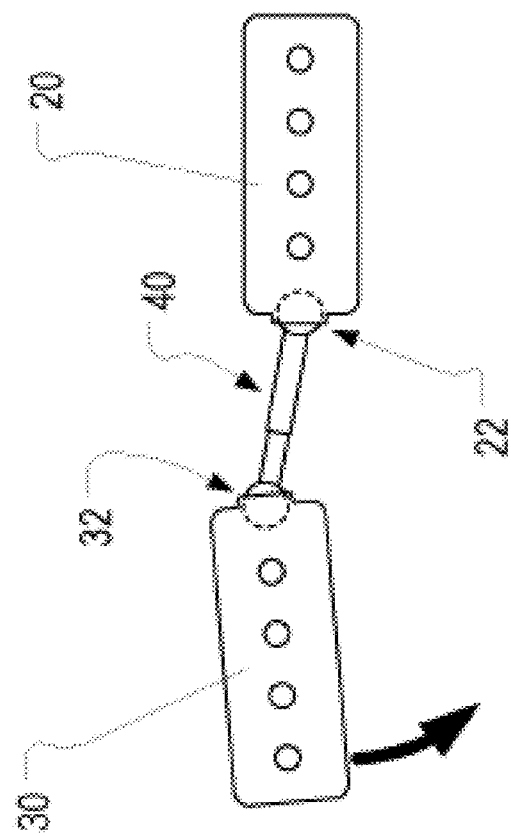

FIG. 3 illustrates adjustment of the bone plate apparatus 10 in the form of movement (in the form of rotation in the direction of the illustrated arrow) of the linking segment 40 and the second plate 30 relative to the first plate 20. The movement is accomplished via rotation of a ball of the linking segment 40 within a socket of the first plate 20 at the articulating joint 22. Similar articulation is possible at the articulating joint 32, as illustrated in FIG. 4, where the second plate 30 is rotated relative to the linking segment 40 and the first plate 20.

In accordance with one or more preferred implementations, the articulated nature of articulating joints of a bone plate apparatus enables positioning of plates of a bone plate apparatus relative to bone portions of a bone (such as portions on opposite sides of a bone fracture).

Figure 5:
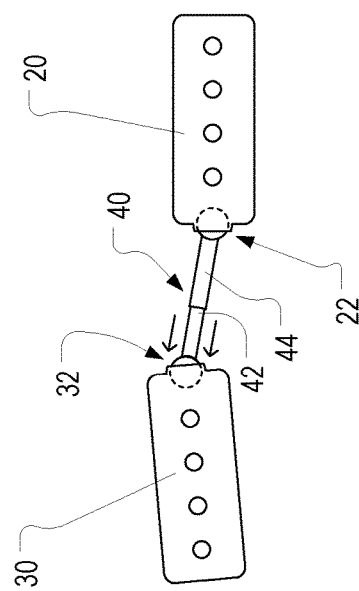
Figure 6:
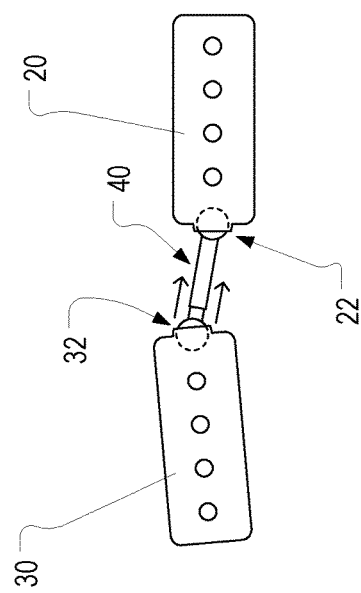

In accordance with one or more preferred implementations, a linking segment is configured for adjustment of its length, which allows for adjustment of a distance between a first plate and a second plate. For example, a length of the linking segment 40 of the bone plate apparatus 10 is adjustable, as illustrated in FIG. 5, in which a length of the linking segment 40 is extended via movement of the inner segment 42 of the linking segment 40 relative to outer segment 44 of the linking segment. A length of the linking segment 40 can similarly be decreased, as illustrated in FIG. 6.

In accordance with one or more preferred implementations, the articulated nature of articulating joints of a bone plate apparatus together with length adjustability of a linking segment enables positioning of plates of a bone plate apparatus relative to bone portions of a bone (such as portions on opposite sides of a bone fracture).

Figure 7:
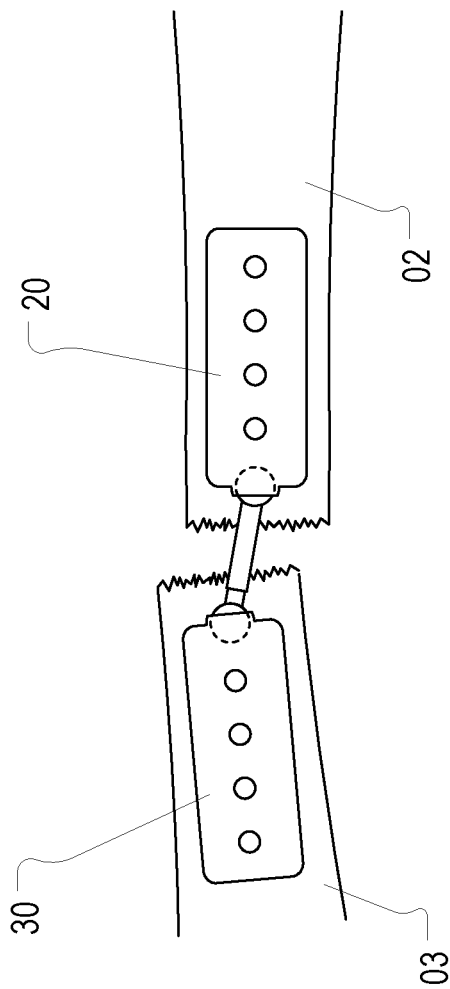
FIG. 7 illustrates how adjustment of the bone plate apparatus of FIG. 1 can facilitate securement to bone portions.

For example, FIG. 7 illustrates how the articulated nature of articulating joints 22,32 of the bone plate apparatus 10 together with length adjustability of the linking segment 40 enables positioning of the plates 20,30 of the bone plate apparatus 10 relative to the bone portions 02,03 of a bone.

Figure 8:
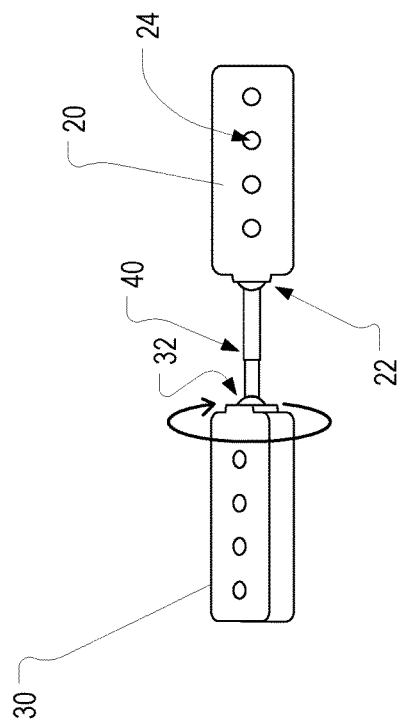
FIG. 8 illustrates adjustment of the bone plate apparatus of FIG. 1.

Although bone plate apparatus have thus far been primarily illustrated with respect to movement through a single plane, as noted above, articulating joints of a bone plate apparatus may be configured to enable movement through two or more planes. For example, FIG. 8 illustrates rotation of the second plate 30 relative to the linking segment 40 and the first plate 20.

Figure 9:
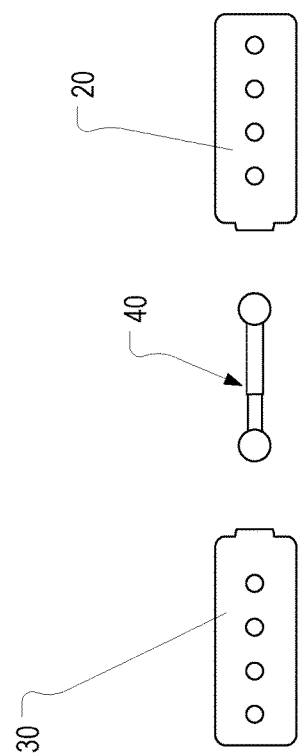
FIG. 9 illustrates detchability of a linking segment from plates of a bone plate apparatus.

In accordance with one or more preferred implementations, a linking segment is configured to be removably connectable or attachable to plates. For example, FIG. 9 illustrates the linking segment 40 disconnected or detached from the first plate 20 and second plate 30 of the bone plate apparatus 10. In accordance with one or more preferred implementations, one or more bone plates may be secured to bone portions without a linking segment attached thereto. Subsequently, a linking segment may be connected to the bone plates. In accordance with one or more preferred implementations, a bone plate may be positioned and secured to a bone portion with a first end of a linking segment connected thereto, and a second end of that linking segment may thereafter be connected to another bone plate (which may be secured to a bone portion either before or after such attachment to the linking segment).

Figure 10:
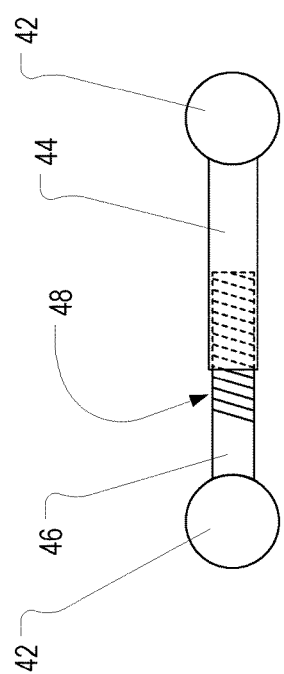
FIGS. 10-11 illustrate features of exemplary linking segments.

As noted hereinabove, in accordance with one or more preferred implementations, a linking segment may be extendible or adjustable so as to have an adjustable length. FIG. 10 illustrates an adjustable linking segment 40 including an inner segment 46 that is sized and dimensioned to be at least partially received within (e.g. to have one end and an extent extending therefrom received within) a hollow outer segment 44. The adjustable linking segment 40 is configured to allow for alteration of an extent of the inner segment 46 received within the outer segment 44. The adjustable linking segment 40 is configured for screw like engagement of the segments 44,46 together with male threading engaging female threading (either segment 44,46 may have either male or female threading). A length of the adjustable linking segment 40 may be adjusted by rotating one of the segments 44,46 relative to the other.

Figure 11:
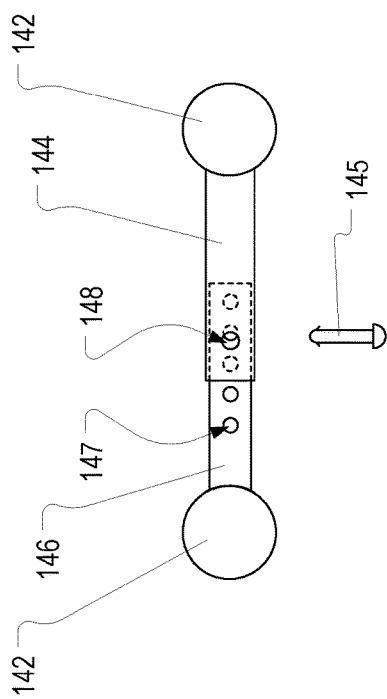

In accordance with one or more preferred implementations, a mechanism may be provided to lock adjustment of a length of an adjustable linking segment. FIG. 11 illustrates an adjustable linking segment 140 which includes an inner segment 146 that is sized and dimensioned to sized and dimensioned to be at least partially received within (e.g. to have one end and an extent extending therefrom received within) a hollow outer segment 144. The adjustable linking segment 140 is configured to allow for alteration of an extent of the inner segment 146 received within the outer segment 144 (e.g. by sliding of the inner segment 146 relative to the outer segment 144.

The inner segment 146 includes a plurality of openings 147, as illustrated in FIG. 11. The inner segment 146 may optionally include similar openings diametrically opposite those illustrated. The outer segment 144 includes an opening 148. The outer segment 144 may optionally include additional openings, and further may include one or more similar openings diametrically opposite the opening 148 that is illustrated, as well as any others. Although in the illustrated implementation the inner segment 146 includes a plurality of openings 147 and the outer segment 144 includes only a single opening 148, in one or more preferred implementations an inner segment may include a single opening with an outer segment including a plurality of openings, or, as just noted, both segments may include a plurality of openings.

The openings 147 of the inner segment 146 and the opening 148 of the outer segment are configured to allow a screw, bolt, pin, or other insert 145 to be inserted to lock adjustment of the inner segment 146 relative to the outer segment 144.

In accordance with one or more preferred implementations, alternative structures and methodologies may be utilized to enable adjustability of the length of a linking segment. For example, a linking segment may comprise a spring, telescoping portions (e.g. three telescoping portions), or other mechanisms for enabling adjustment.

In accordance with one or more preferred implementations, alternative structures and methodologies may be utilized to enable locking of length adjustment of a linking segment.

In accordance with one or more preferred implementations, a linking segment may be a fixed length linking segment.

Figure 12:
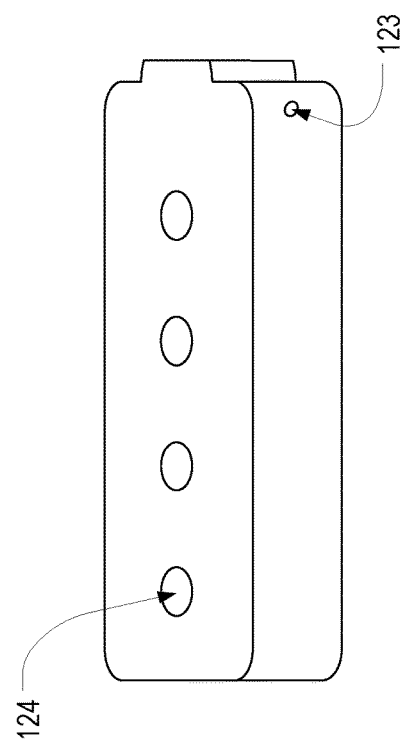
FIG. 12-15B illustrate components of an exemplary bone plate apparatus including a locking mechanism for an articulating joint.
Figure 13A:
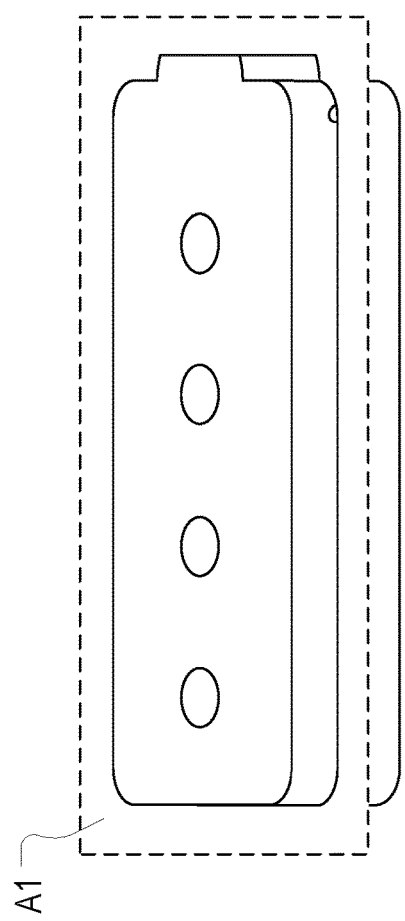
Figure 13B:
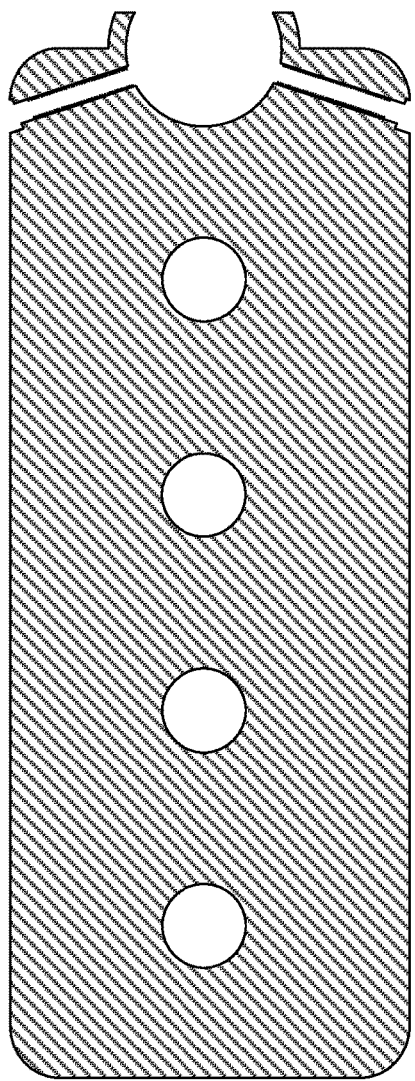
Figure 14:
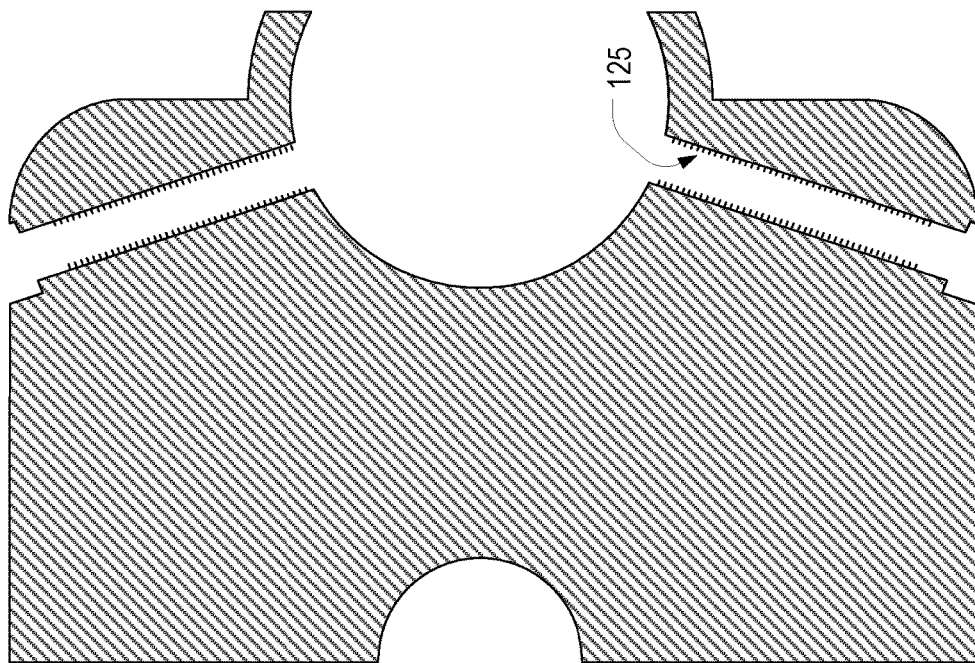
Figure 15A:
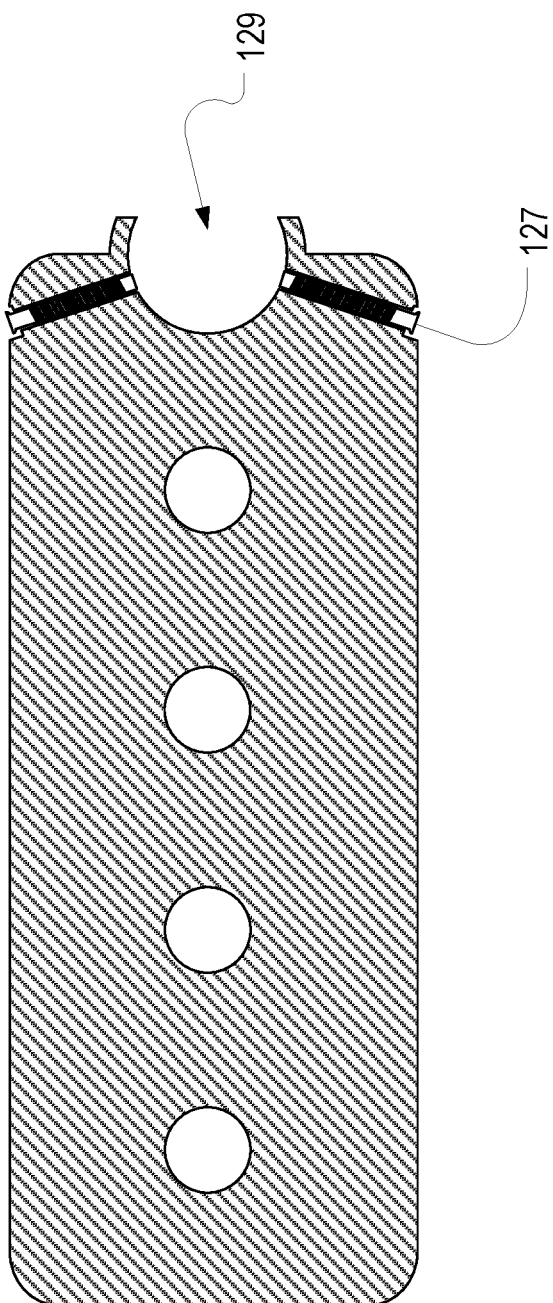

In accordance with one or more preferred implementations, a bone plate apparatus is configured to allow for locking of adjustment at an articulation joint. For example, FIG. 12 illustrate a plate 120 which includes openings 123 of a passageway for insertion of a screw, nut, pin, or bolt for locking of adjustment at an articulation joint comprising a ball and socket joint. FIG. 13B illustrates a cross-sectional view of the plate 120 at plane A1 illustrated in FIG. 13A. FIG. 14 is a close up cross-sectional view of the plate 120 at plane A1 which includes a fanciful representation of threading 125 of passageways of the plate 120, and FIG. 15A is a fanciful illustration providing the same cross-sectional view of the plate 120 at plane A1, but further including fanciful illustrations of screws 127 (which are not illustrated in cross-section).

Figure 15B:
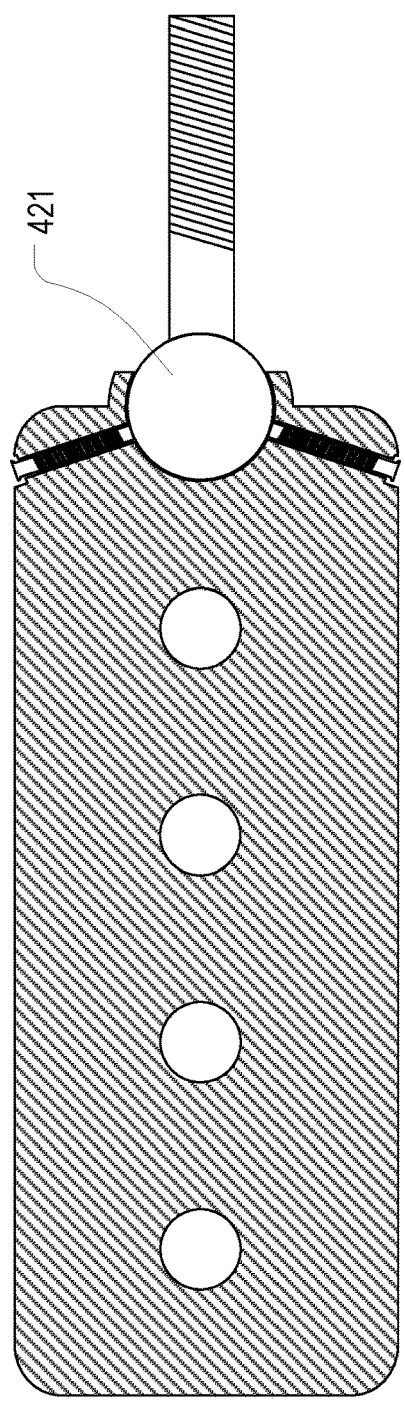

FIG. 15B is another fanciful illustration providing the same cross-sectional view of the plate 120 at plane A1, but further including fanciful illustrations of a portion of a linking segment which includes a ball member 421 (the linking segment is not illustrated in cross-section) sized to mate with and be received and retained within a socket 129 of the plate 120.

Figure 16:
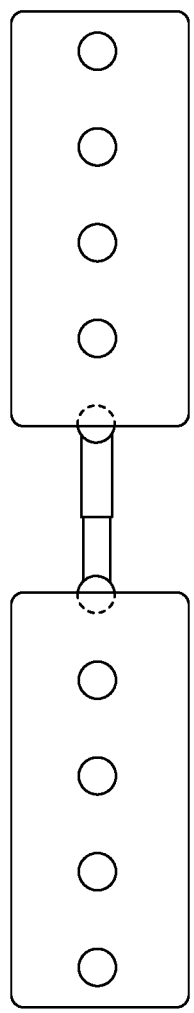
FIG. 16 illustrates another exemplary bone plate apparatus.

It will be appreciated that the illustrations referenced hereinabove are largely fanciful illustrations designed to assist in providing an overview of features in accordance with one or more preferred implementations. Many preferred implementations depart from the specifically illustrated dimensions and structure. For example, FIG. 16 is a fanciful illustration of an implementation utilizing smaller ball and socket joints, as compared to the implementation illustrated in FIG. 1.

Exemplary Preferred Implementations Utilizing Mating Curved Surfaces

In accordance with one or more preferred implementations, a bone plate apparatus includes one or more curved concave surfaces and one or more curved convex surfaces, with the curved concave surfaces being configured to mate in adjustable engagement with the curved convex surfaces.

Figure 17A:
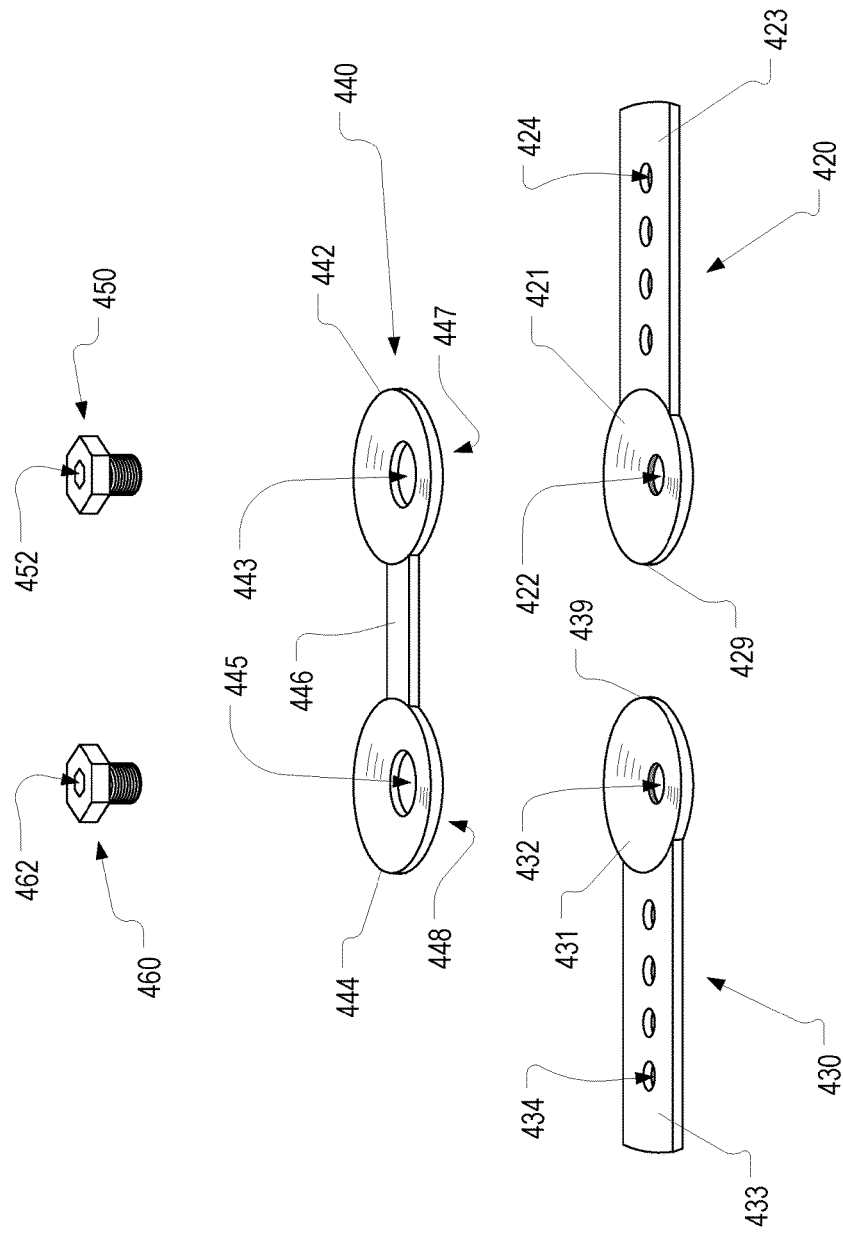
FIGS. 17A-30 illustrate exemplary features of bone plate apparatus utilizing mating curved surfaces.
Figure 17B:
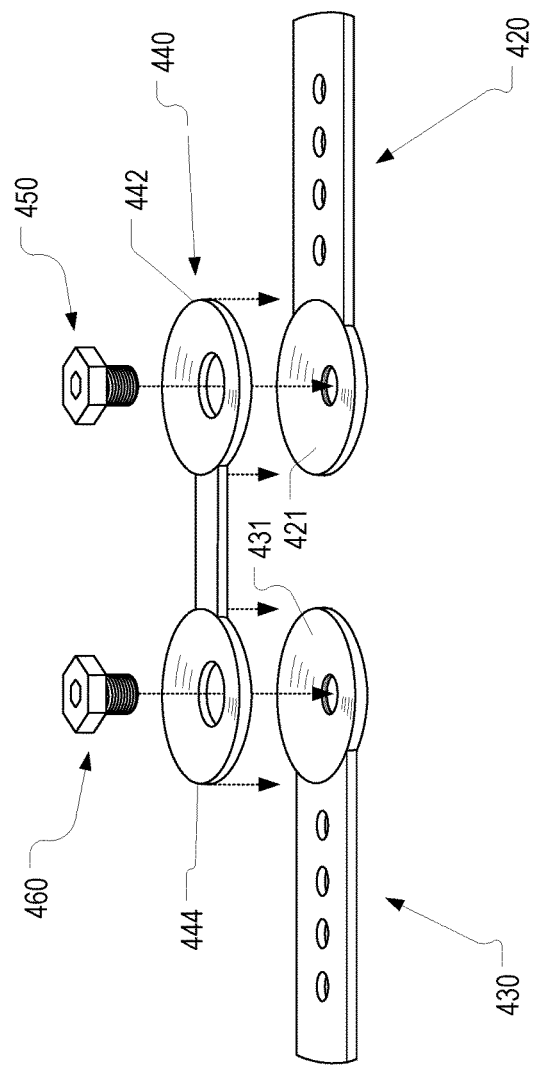

For example, FIG. 17A illustrates components of a bone plate apparatus 410 which includes curved concave and convex surfaces configured to mate in adjustable engagement, and FIG. 17B is an exploded view of the bone plate apparatus 410.

The bone plate apparatus 410 includes a first plate 420 comprising a plate portion 423 which includes a plurality of openings 424 defined therethrough for use in receiving bone screws for securement of the first plate 420 to bone. The first plate 420 further includes a curved portion 429 which includes a curved concave upper face 421 and a central opening defined in the curved concave upper face 421 which is an opening of a central passageway 422 defined through the curved portion 429 of the first plate 420 (although openings and passageways may be referred to herein for purposes of clarity as "central", in accordance with one or more preferred implementations such a central opening or passageway does not necessarily have to be in a center of a curved portion or a curved surface or face). The curved portion 429 further includes a curved convex lower face, with a central opening defined therein being an opposite opening of the central passageway 422 defined through the curved portion 429 of the first plate 420. One or more wall surfaces defining the central passageway 422 include threading for threaded engagement with a screw or bolt.

The bone plate apparatus 410 similarly includes a second plate 430 comprising a plate portion 433 which includes a plurality of openings 434 defined therethrough for use in receiving bone screws for securement of the second plate 430 to bone. The second plate 430 further includes a curved portion 439 which includes a curved concave upper face 431 and a central opening defined in the curved concave upper face 431 which is an opening of a central passageway 432 defined through the curved portion 439 of the second plate 420. The curved portion 439 further includes a curved convex lower face, with a central opening defined therein being an opposite opening of the central passageway 432 defined through the curved portion 439 of the second plate 430. One or more wall surfaces defining the central passageway 432 include threading for threaded engagement with a screw or bolt.

The bone plate apparatus 410 further includes a linking segment 440 comprising first and second curved portions 442,444 joined together by a linking portion 446. The linking portion 446 is illustrated as a fixed length, but in accordance with one or more preferred implementations, an adjustable length linking portion may be utilized.

The first curved portion 442 of the linking segment 440 includes a curved concave upper face and a central opening defined in the curved concave upper face which is an opening of a central passageway 443 defined through the first curved portion 442 of the linking segment 440. The curved portion 442 further includes a curved convex lower face 447, with a central opening defined therein being an opposite opening of the central passageway 443 defined through the first curved portion 442 of the linking segment 440. A diameter of the central passageway 443 defined through the first curved portion 442 of the linking segment 440 is greater than a diameter of the central passageway 422 defined through the curved portion 429 of the first plate 420.

The second curved portion 444 of the linking segment 440 includes a curved concave upper face and a central opening defined in the curved concave upper face which is an opening of a central passageway 445 defined through the second curved portion 444 of the linking segment 440. The curved portion 444 further includes a curved convex lower face 448, with a central opening defined therein being an opposite opening of the central passageway 445 defined through the second curved portion 444 of the linking segment 440. A diameter of the central passageway 445 defined through the second curved portion 444 of the linking segment 440 is greater than a diameter of the central passageway 432 defined through the curved portion 439 of the second plate 430.

The bone plate apparatus 410 further includes first and second screws 450,460 configured for securement of the linking segment 440 to the first and second plates 420,430. The first and second screws 450,460 include tool indentations 452,462 shaped and dimensioned for engagement with a tool, e.g. a hex key tool.

Figure 18A:
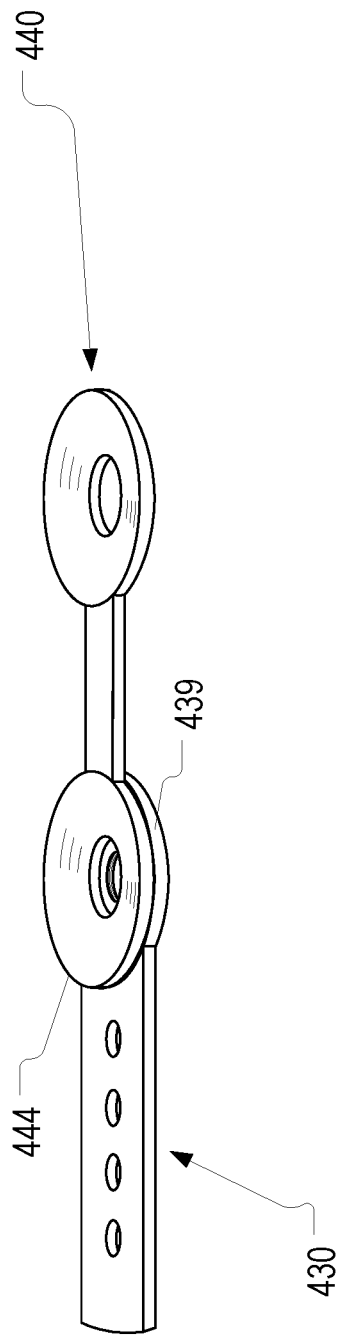

The curved concave upper faces 421,431 of the first and second plate 420,430 are shaped and dimensioned to mate in adjustable engagement with the curved convex lower faces 447,448 of the linking segment 440, in a manner very similar to nested spoons where a bottom surface of a first spoon sits within and engages a top surface of a second spoon. For example, FIG. 18A illustrates mating of the curved concave upper face 431 of the curved portion 439 of the second plate 430 with the curved convex lower face 448 of the curved portion 444 of the linking segment 440. These faces 431,448 are mated in adjustable engagement, with the curved portion 444 of the linking segment 440 sitting within and engaging the curved portion 439 of the second plate 430. This adjustable engagement allows for movement of the linking segment 440 and second plate 430 relative to one another, as illustrated in FIG. 18B, with a range of motion of such movement being limited by the physical geometries of the curved concave upper face 431 of the curved portion 439 of the second plate 430 and the curved convex lower face 448 of the curved portion 444 of the linking segment 440.

Figure 18B:
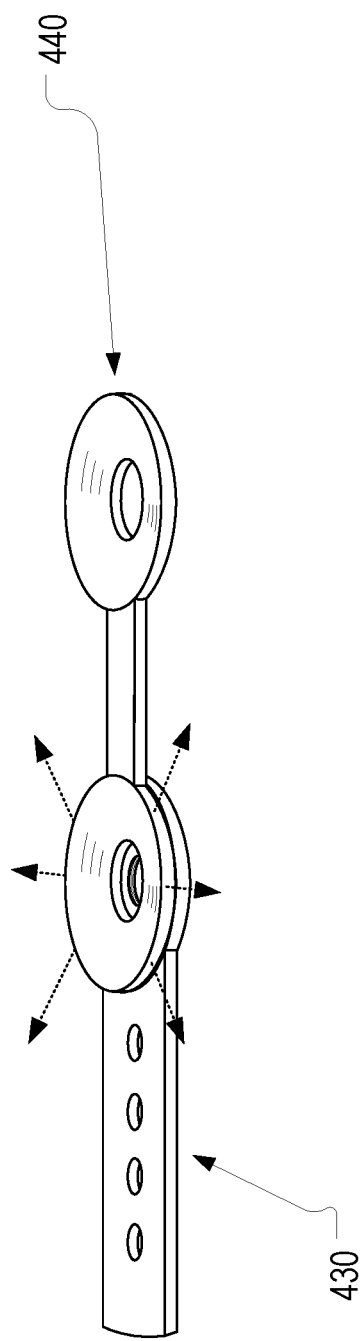
Figure 18C:
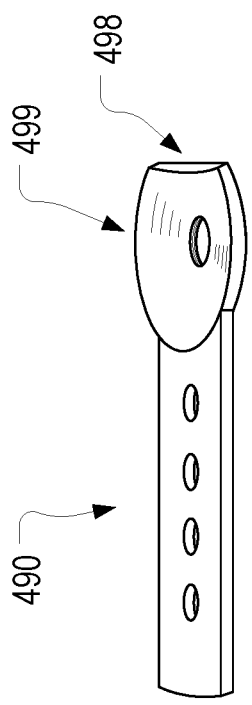
Figure 18D:
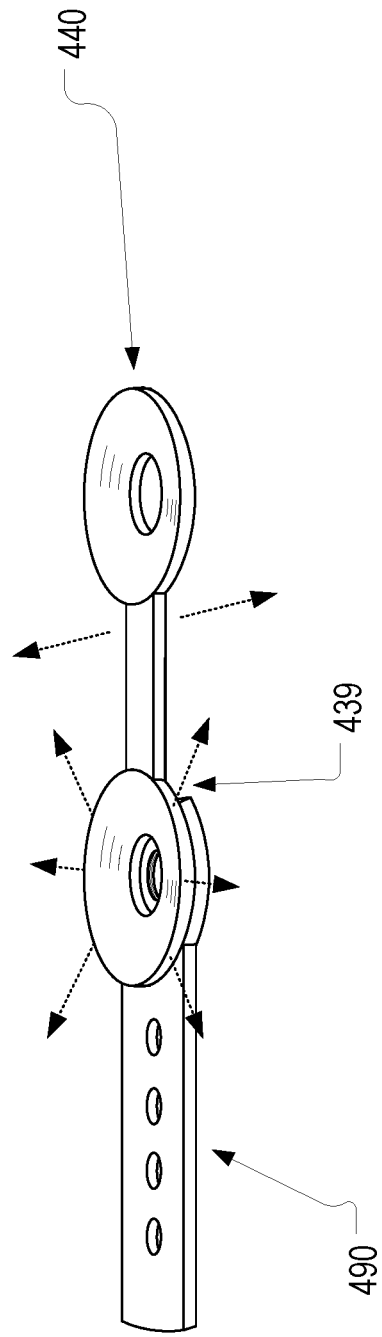

It will be appreciated from the illustration in FIG. 18B that the specific geometry of one or more components may sometimes hinder free movement. For example, an edge of the curved portion 439 of the second plate 430 might inhibit downward movement of an opposite end of the linking segment 440. In accordance with one or more preferred implementations, a geometry of one or more curved portions is configured to facilitate a preferred range of motion (e.g. increase range of motion as compared to the second plate 430 and the linking segment 440. For example, FIG. 18C illustrates an exemplary implementation involving a plate 490 which includes a curved portion 499 having a partial cutout 498 which is configured to increase a potential range of motion of a linking segment 440 mated therewith, as illustrated in FIG. 18D, in which downward movement of an opposite end of the linking segment 440 is facilitated by the partial cutout 498.

Figure 18E:
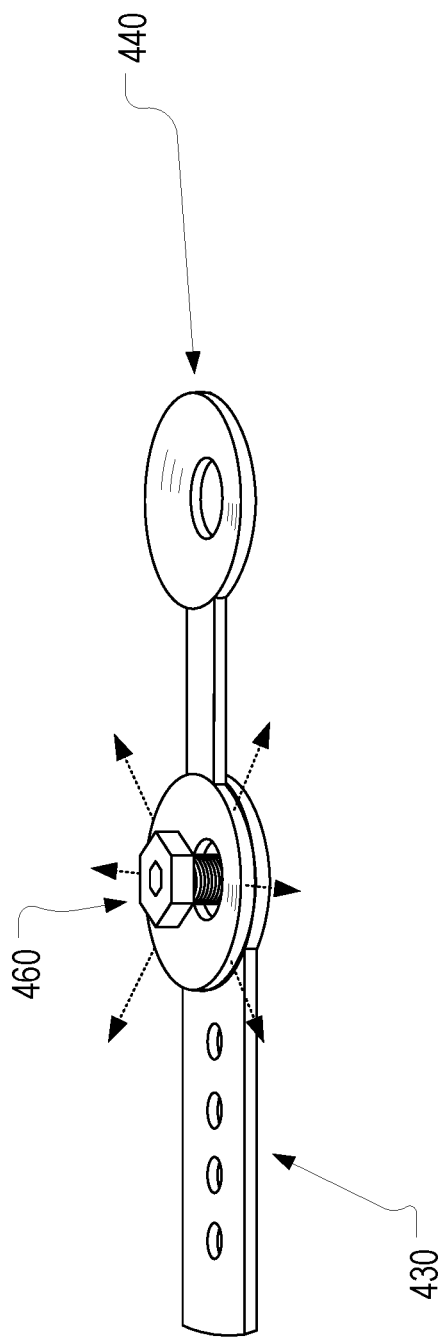

Returning to the plate 430 illustrated in FIG. 18B, movement of the plate 430 relative to the linking segment 440 can be further limited via insertion of the screw 460 through the central passageway 445 defined through the second curved portion 444 of the linking segment 440 and into the opening defined in the concave upper face 431 of the curved portion 439 of the second plate 430, as illustrated in FIG. 18E. The screw 460 can be screwed into the second plate 430 via threaded engagement of threads of the screw 460 with threading of one or more wall surfaces defining the central passageway 432 of the curved portion 439 of the second plate.

As noted above, a diameter of the central passageway 445 defined through the second curved portion 444 of the linking segment 440 is greater than a diameter of the central passageway 432 defined through the curved portion 439 of the second plate 430. The difference in diameter (and in particular the difference in diameter between the central passageway 445 defined through the second curved portion 444 of the linking segment 440 and the screw 460) allows for limited movement of the linking segment 440 relative to the second plate 430 even when the screw 460 is received within the central passageway 445 defined through the second curved portion 444 of the linking segment 440. The extent of movement that is allowed depends on the difference in diameter (as well as the geometry of mated curved surfaces), and in various preferred implementations various sized passageways and screws (and various geometries of curved surfaces) are utilized to achieve various different ranges of motion.

Figure 18F:
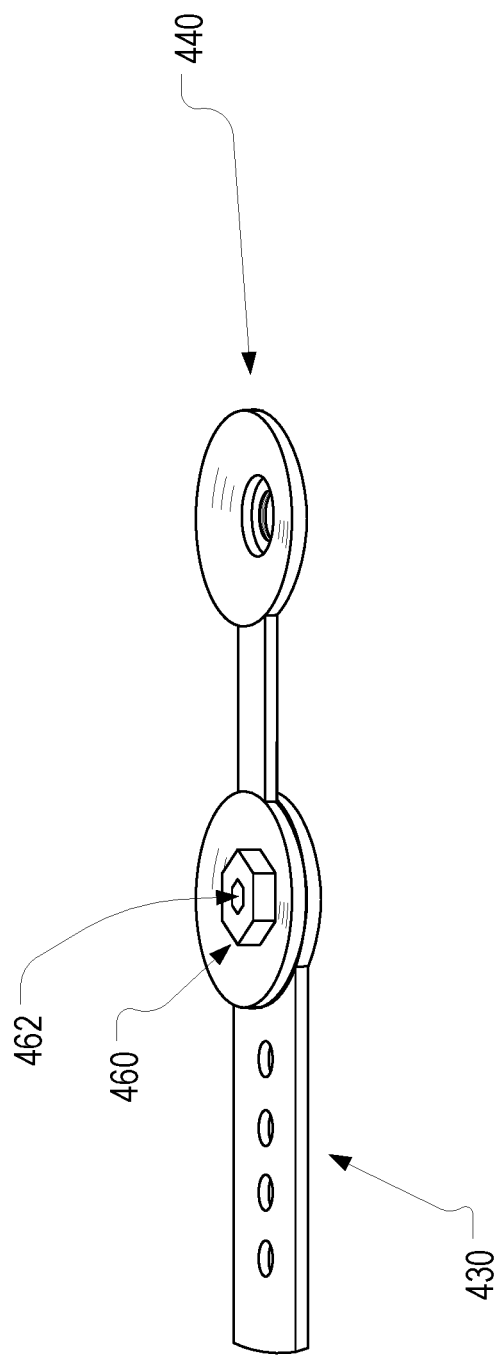

The screw 460 can be screwed further into the threaded central passageway 445 of the second plate 430 via use of a hex key tool that is inserted into the tool indentation 462 and used to rotate the screw 460. Once the screw 460 has been screwed in sufficiently far, the screw 460 will serve to force the curved concave upper face 431 of the curved portion 439 of the second plate 430 together with the curved convex lower face 448 of the curved portion 444 of the linking segment 440, thus inhibiting movement of the linking segment 440 relative to the second plate 430, as illustrated in FIG. 18F. The screw 460 can thus be used to lock the linking segment 440 and the second plate 430 relative to one another.

Figure 19:
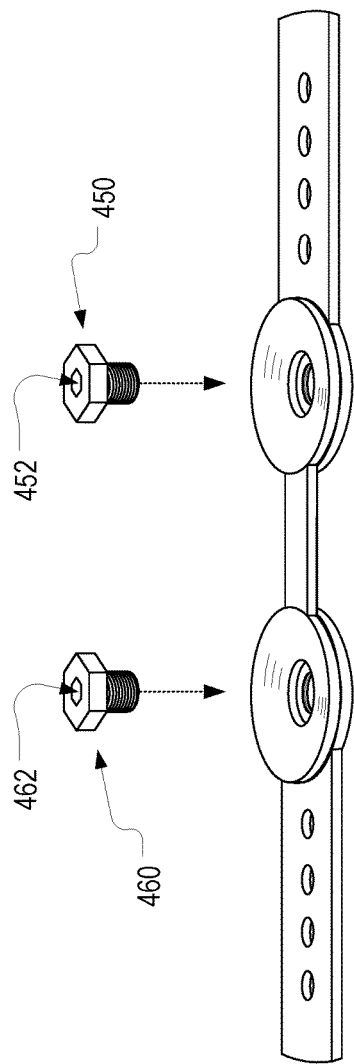
Figure 20:
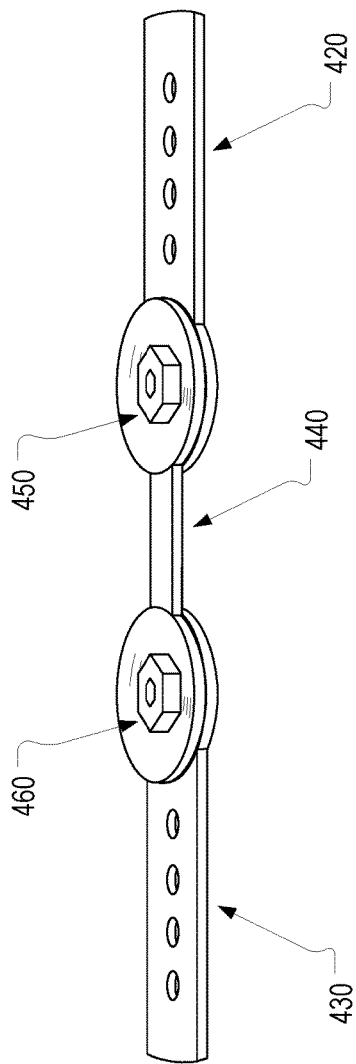
Figure 21:
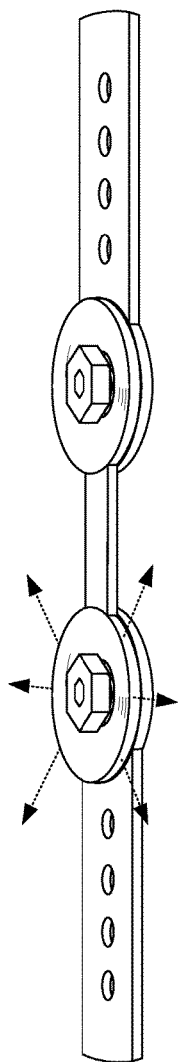

The screw 450 can similarly be used to secure the linking segment 440 to the first plate 420, as illustrated in FIG. 19. The screws 450,460 can be screwed in to lock the configuration of the bone plate apparatus 410, as illustrated in FIG. 20 (i.e. screw 462 can prevent movement of the linking segment 440 and the second plate 430 relative to one another, and screw 452 can prevent movement of the linking segment 440 and the first plate 420 relative to one another). If further adjustment is desired, one or both of the screws 450,460 can be loosened to enable movement of one or both of the plates 420,430 relative to the linking segment 440, as illustrated in FIG. 21.

Bone plate apparatus 410 is an exemplary bone plate apparatus that includes curved concave and convex surfaces configured to mate in adjustable engagement. The bone plate apparatus 410 is exemplifies features in accordance with one or more preferred implementations, and other implementations may depart from the specifically illustrated dimensions and structure.

Figure 22:
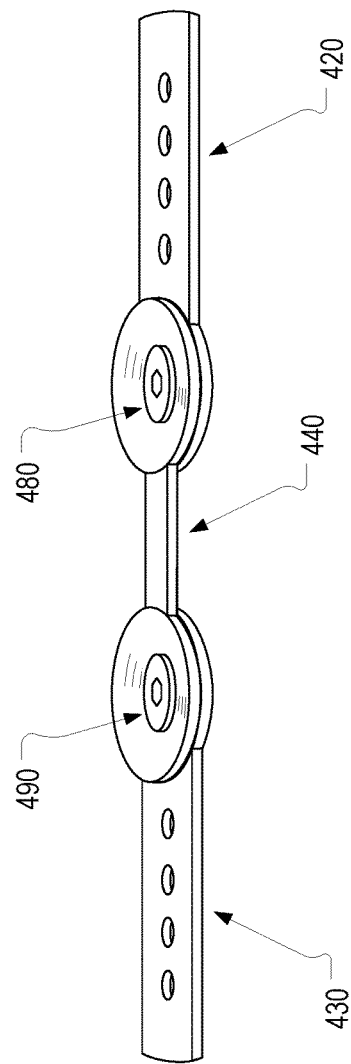

For example, FIG. 22 illustrates use of screws 480,490 which include a head having a slimmer head as compared to screws 450,460. In accordance with various preferred implementations, various fasteners including screws, bolts, pins, etc. may be utilized to secure a plate to a linking segment (or even to another plate).

Further, bone plate apparatus 410 illustrates upper surfaces of curved portions of plates mating with lower surfaces of curved portions of a linking segment, it will be appreciated that this could well be reversed, with lower surfaces of curved portions of plates mating with upper surfaces of curved portions of a linking segment (e.g. with a linking segment including a smaller opening and a threaded passageway). Each side of a linking segment may be configured to mate in a different way as well, with one lengthwise side having a curved portion configured to mate on top of a curved portion of a plate, and the other lengthwise side having a curved portion configured to mate on the bottom of a curved portion of a plate. Curved portions of bone plates could even be configured to mate with one another.

Also, in accordance with various preferred implementations, curved portions of various shapes may be utilized. For example, while bone plate apparatus 410 includes curved portions 429,439,442,444 having a generally circular shape, curved portions having various other shapes may be utilized, such as a more elongated shape more closely resembling a spoon.

As an exemplary comparison, FIGS. 23-26 illustrate first and second curved portions 510,520 having a generally circular shape, and FIGS. 27-30 illustrate third and fourth curved portions 530,540 having a more elongated shape.

Figure 24:
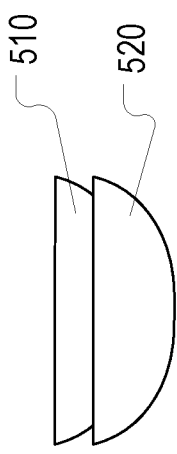
Figure 26:
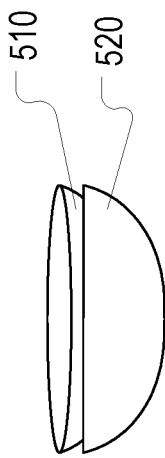
Figure 23:
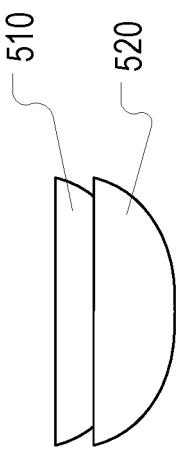
Figure 25:
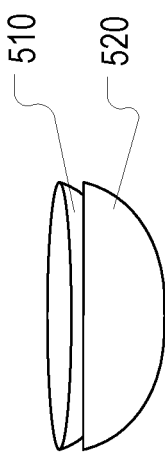

FIGS. 23-24 illustrate the first curved portion 510 nested within the second curved portion 520, with FIG. 23 being a side view and FIG. 24 being a front view. FIGS. 25-26 illustrate the same first and second curved portions 510,520, but the first curved portion 510 has been adjusted relative to the second curved portion 520, with FIG. 25 being a side view and FIG. 26 being a front view.

Figure 28:
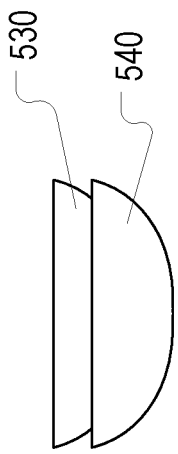
Figure 30:
Figure 27:
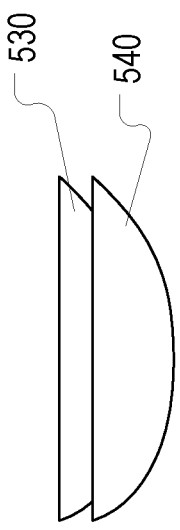
Figure 29:

FIGS. 27-28 illustrate the third curved portion 530 nested within the fourth curved portion 540, with FIG. 27 being a side view and FIG. 28 being a front view. FIGS. 29-30 illustrate the same third and fourth curved portions 530,540, but the third curved portion 530 has been adjusted relative to the fourth curved portion 540, with FIG. 29 being a side view and FIG. 30 being a front view.

Figure 31:
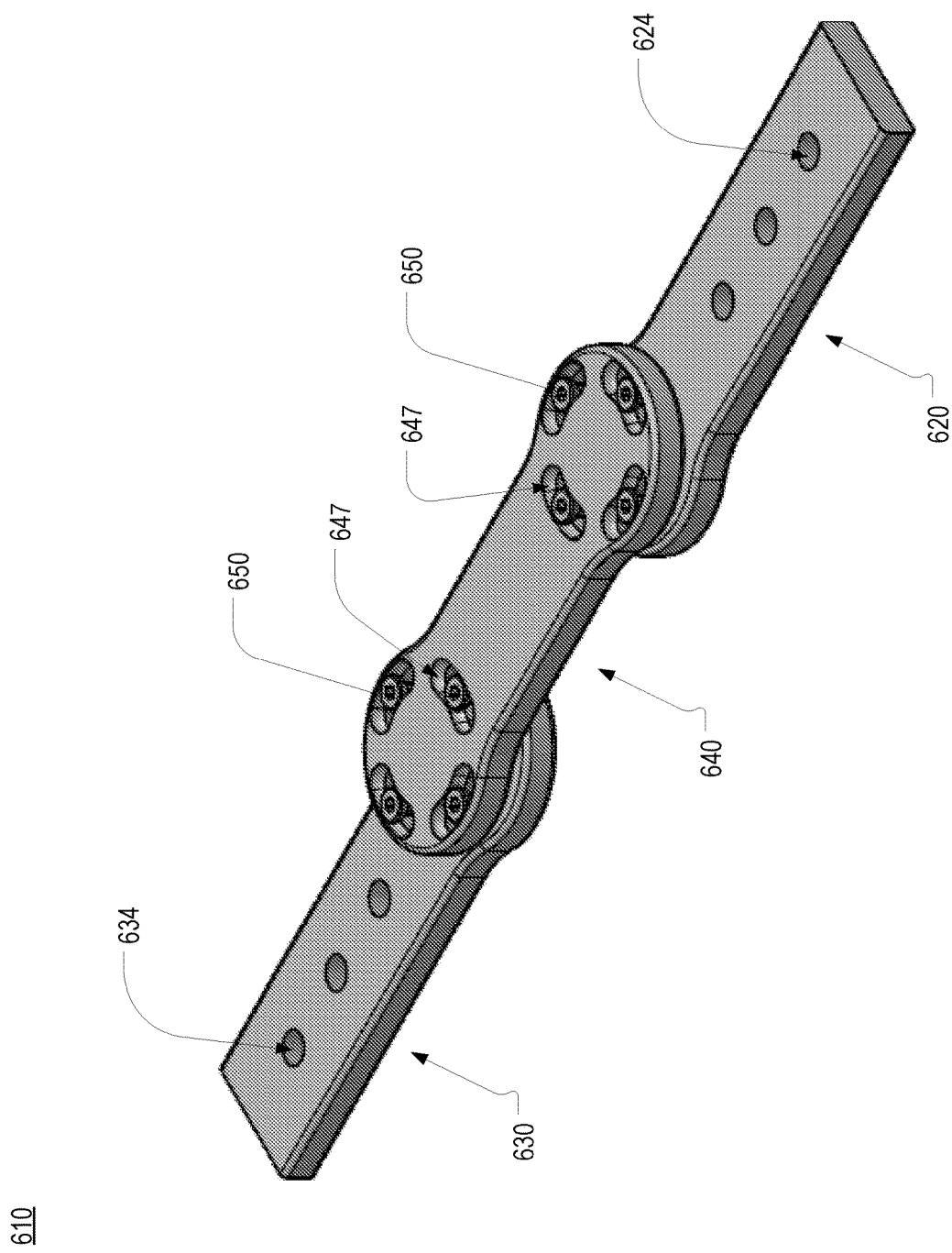
FIGS. 31-35 illustrate exemplary features of a bone plate apparatus utilizing channels enabling rotative movement.
Figure 32:
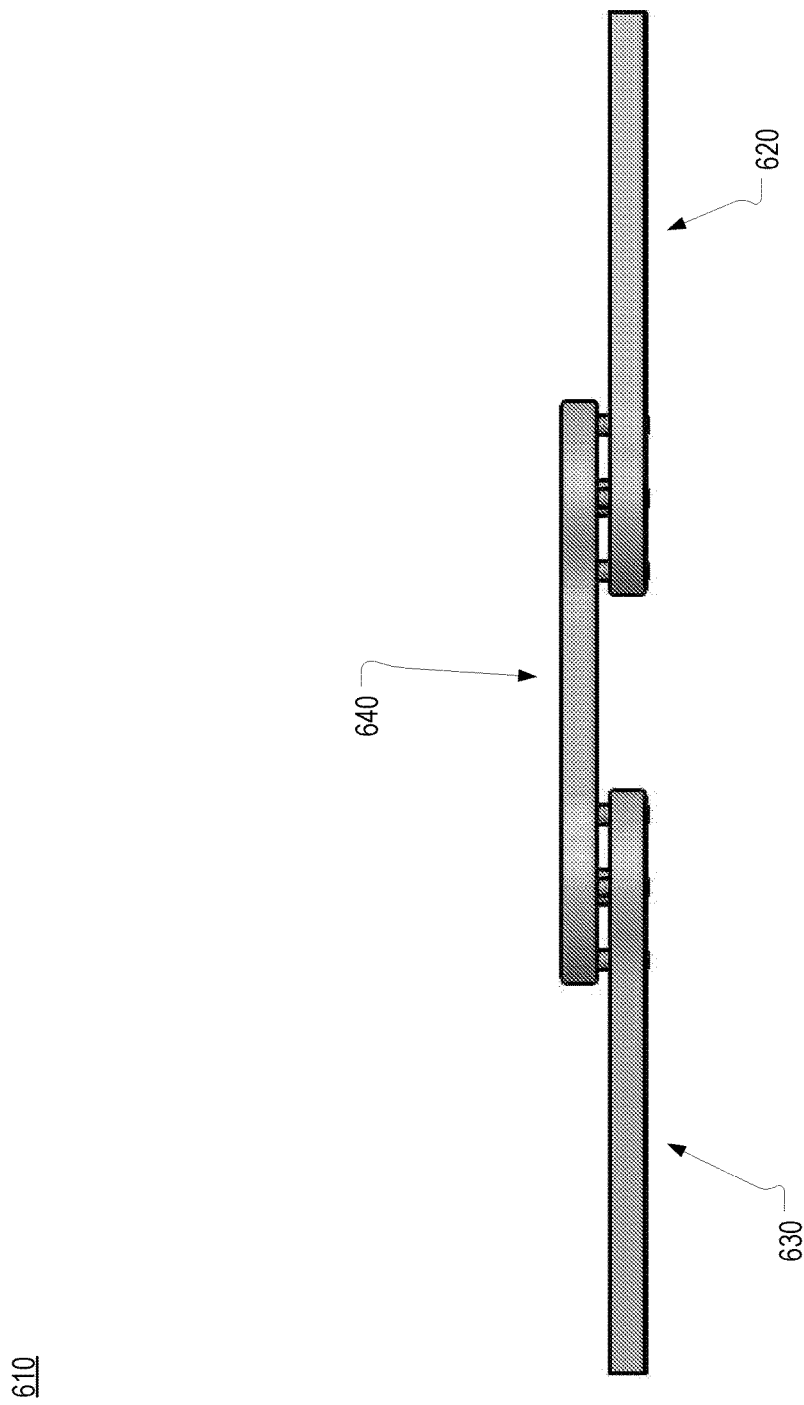
Figure 33:
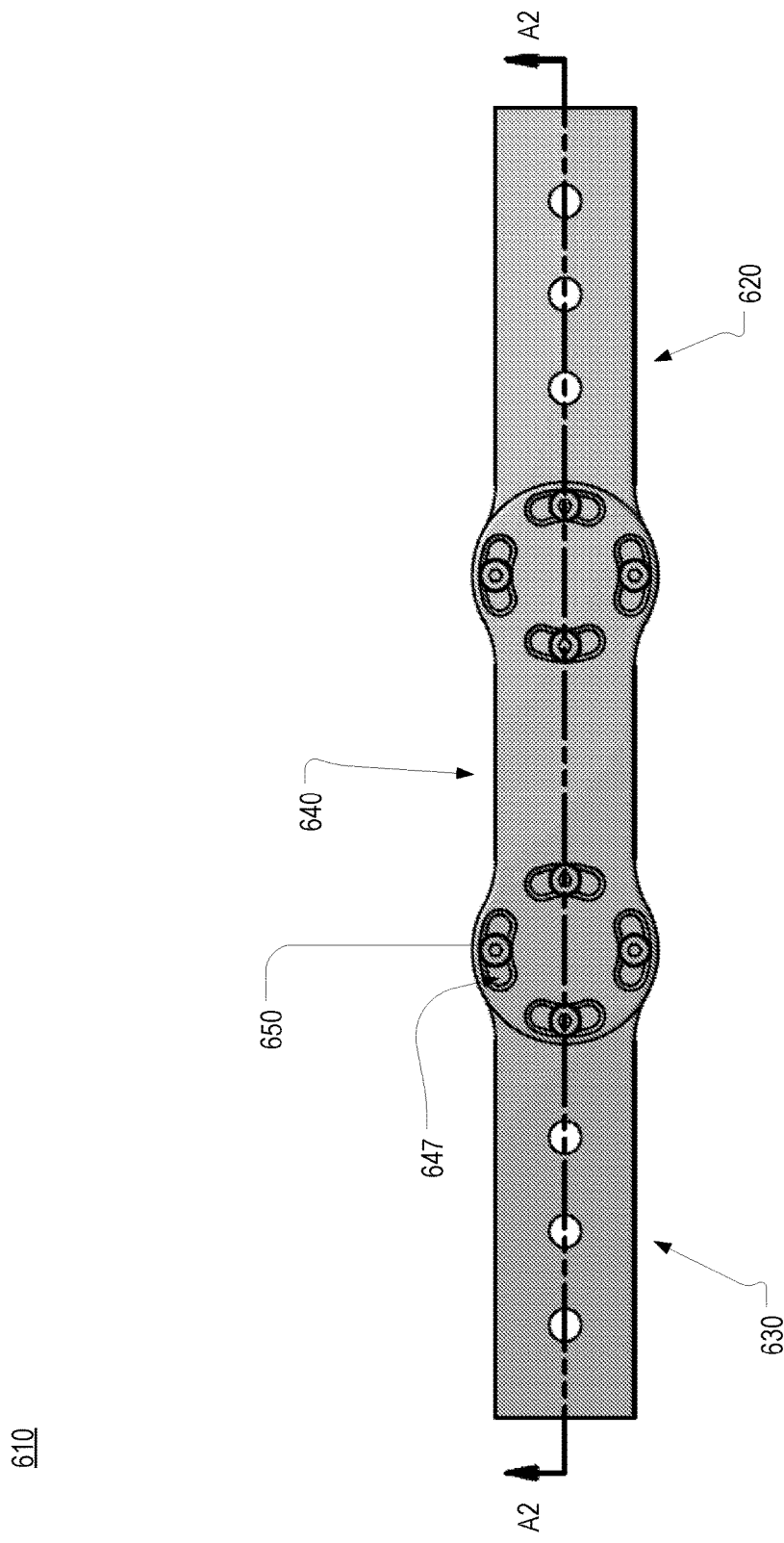

Exemplary Preferred Implementations Utilizing Channels Enabling Rotative Movement FIG. 31 illustrates another bone plate apparatus 610 in accordance with one or more preferred implementations. FIG. 32 is a side view of the bone plate apparatus 610, FIG. 33 is a top view of the bone plate apparatus 610, FIG. 34 is a cross-sectional view of the bone plate apparatus 610 along line A2 illustrated in FIG. 33, and FIG. 35 is a close-up cross-sectional view of the bone plate apparatus 610 showing the portion of the bone plate apparatus 610 within box B of FIG. 34.

The bone plate apparatus 610 includes a first plate 620, a second plate 630, and a linking segment 640. The first plate 620 includes a plurality of openings 624 defined therethrough for use in receiving bone screws for securement of the first plate 620 to bone, and the second plate 630 similarly includes a plurality of openings 634 defined therethrough for use in receiving bone screws for securement of the second plate 630 to bone.

The linking segment 640 includes a plurality of openings each providing access to a channel 647 having sloped walls that generally slope inward moving downward from a top side of the linking segment 640. Each channel 647 is open at a bottom thereof providing access to a respective channel passageway defined through the linking segment 640. Each channel 647 is shaped and dimensioned to accommodate and receive a head of a screw, with the inwardly sloping walls serving to prevent further passage of the head of the screw thus preventing a screw such as one of the screws 650 from traveling further within the corresponding channel passageway defined through the linking segment 640.

Figure 34:
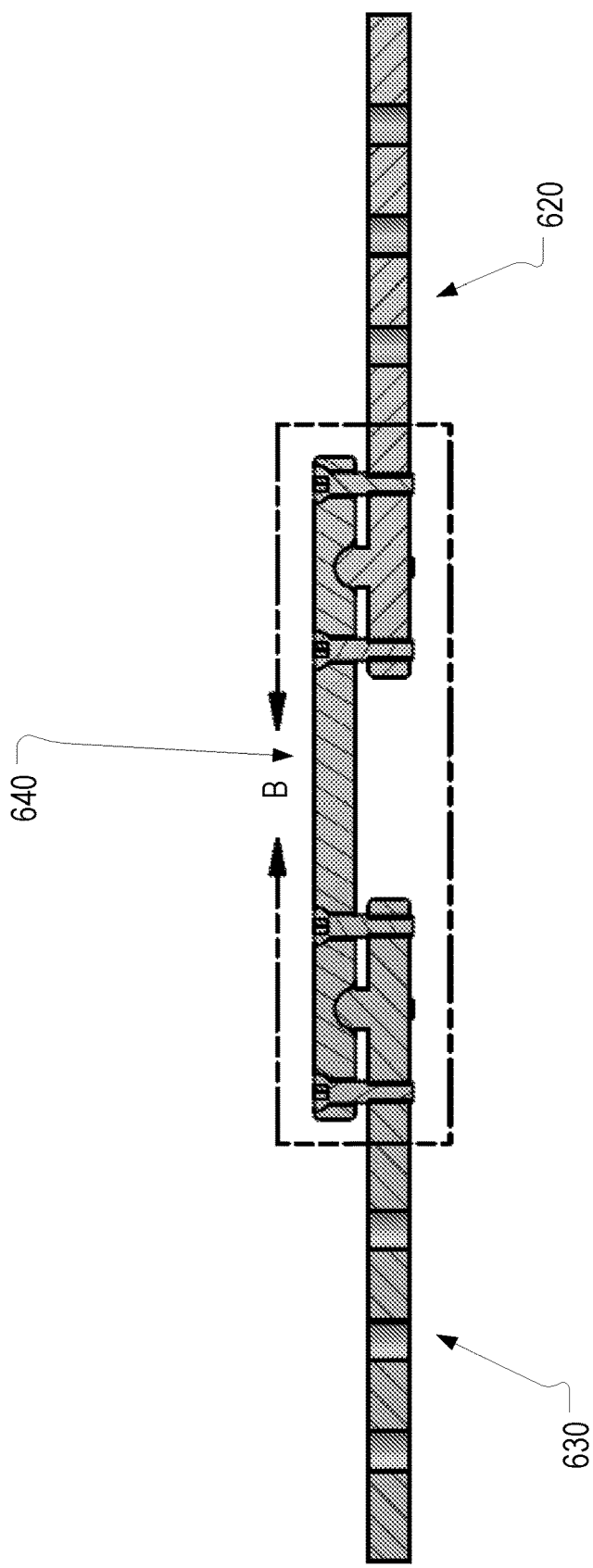
Figure 35:
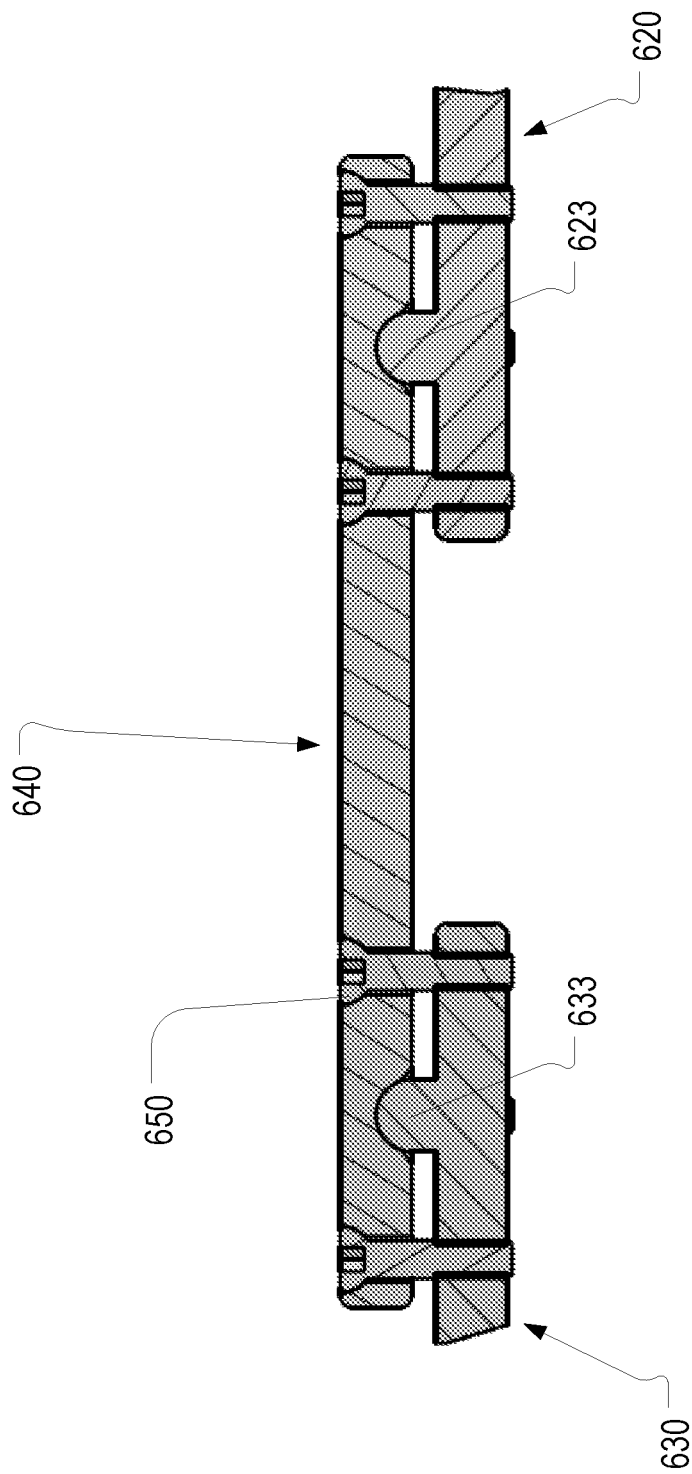

Each plate 620,630 includes four threaded screw receiving channels configured to receive and engage a screw 650, as can be seen in FIG. 34. These screw receiving channels may be passageways defined through the entire plate, or may only be defined partially therethrough.

The channels 647 and the corresponding channel passageways are curved to allow for rotative movement of a plate 620,630 relative to the linking segment 640 even when a screw 650 is received within every channel 647 and channel passageway. Such rotative movement is facilitated by projecting nubs 623,633 of the plates 620,630 received within indentations However, a screw 650 received within a channel 647 and channel passageway may be tightened to prevent such rotative movement.

Although the linking segment 640 is illustrated as including four channels 647 on each side, and each plate 620,630 correspondingly includes four threaded screw receiving channels, in accordance with one or more preferred implementations, a different number of channels may be utilized for some of these elements (for example, one side of a linking segment and a plate might both have five channels). Further, a correspondence between a number of channels on a side of a linking segment and a number of channels of a plate may not hold (for example, one side of a linking segment might have six channels while a plate might have four channels, or one side of a linking segment might have four channels while a plate might have six channels).

Exemplary Preferred Implementations Utilizing Orientation Adjustment Pins

Figure 36:
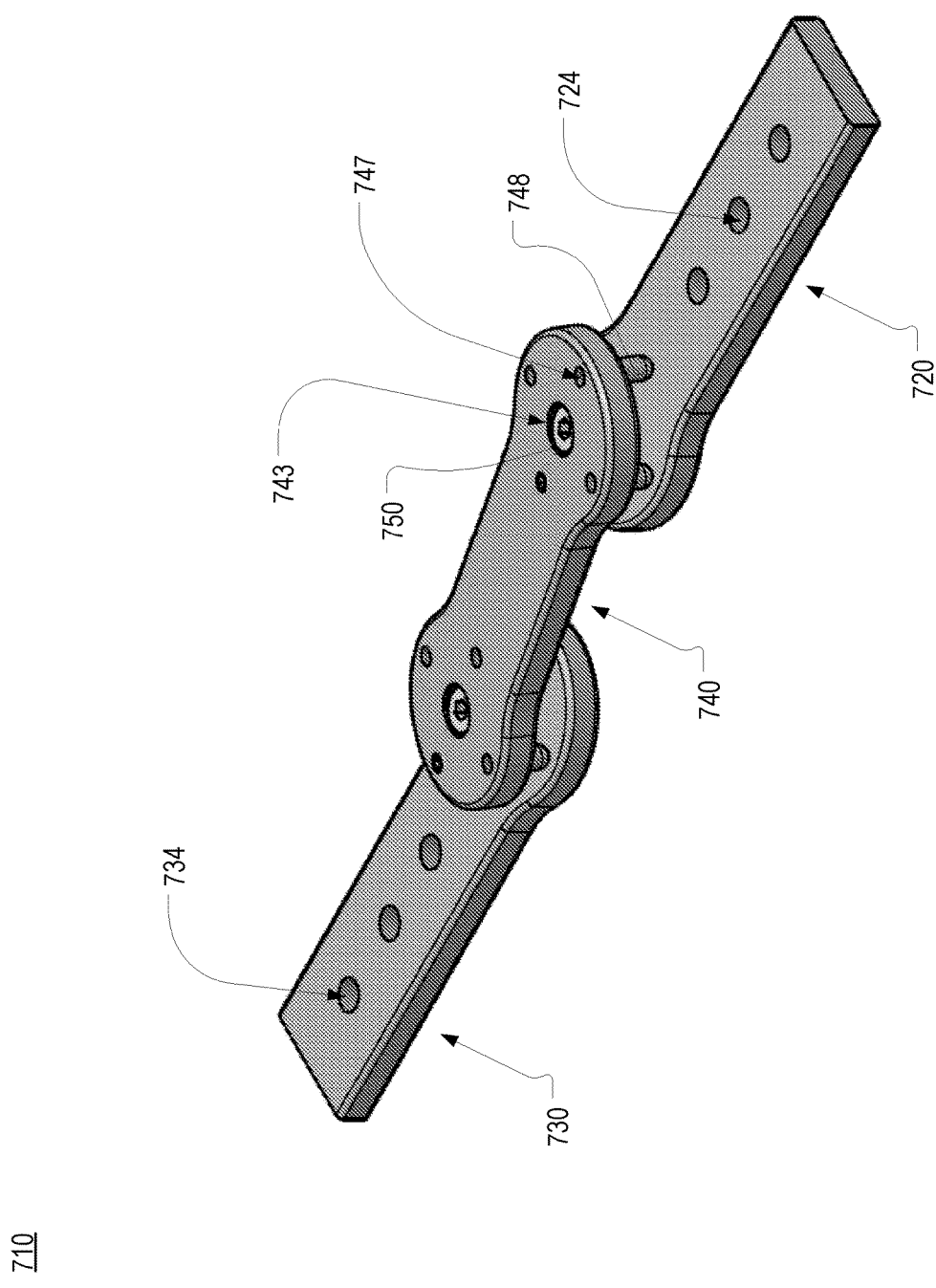
FIGS. 36-40 illustrate exemplary features of a bone plate apparatus utilizing orientation adjustment pins.
Figure 37:
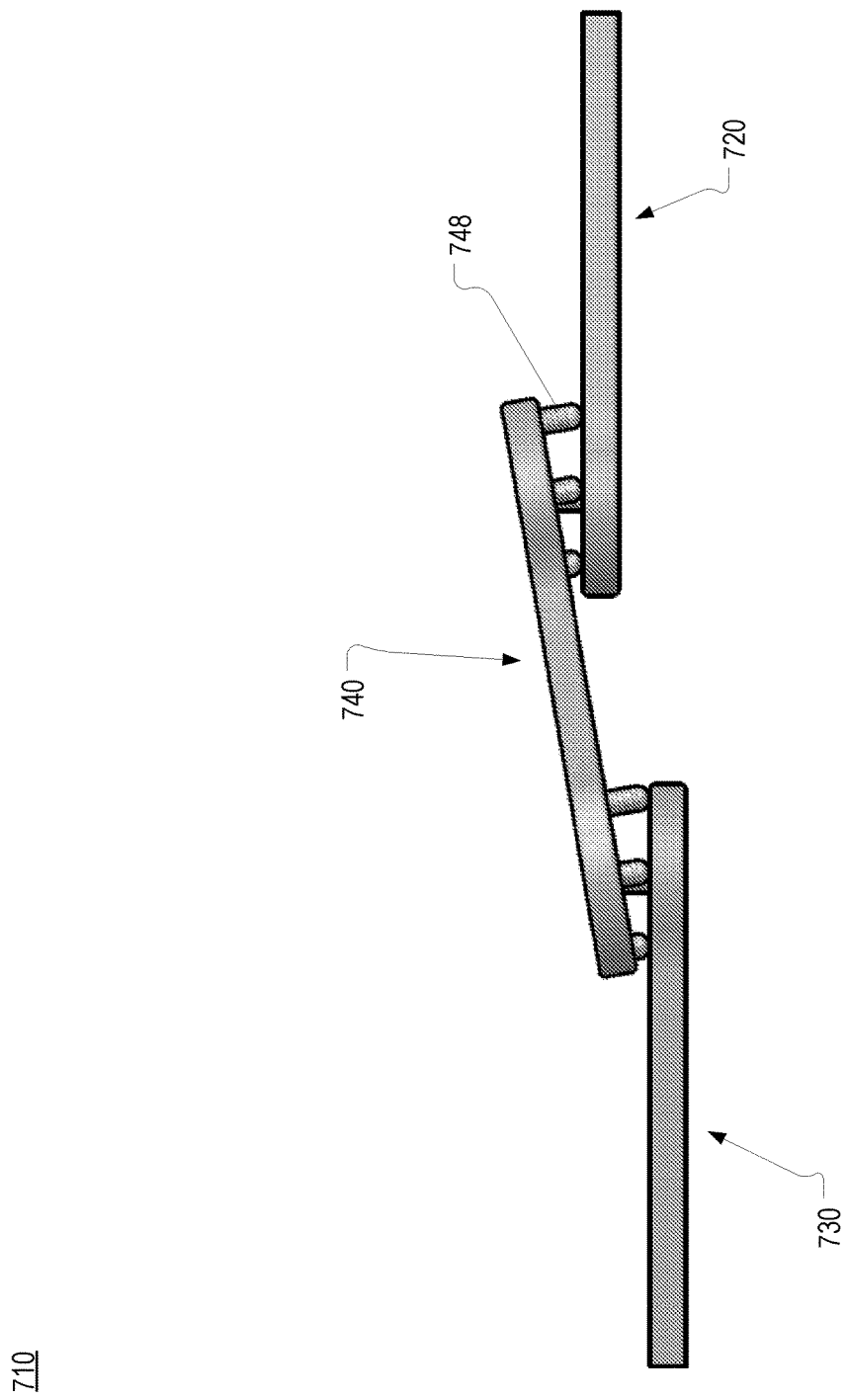
Figure 38:
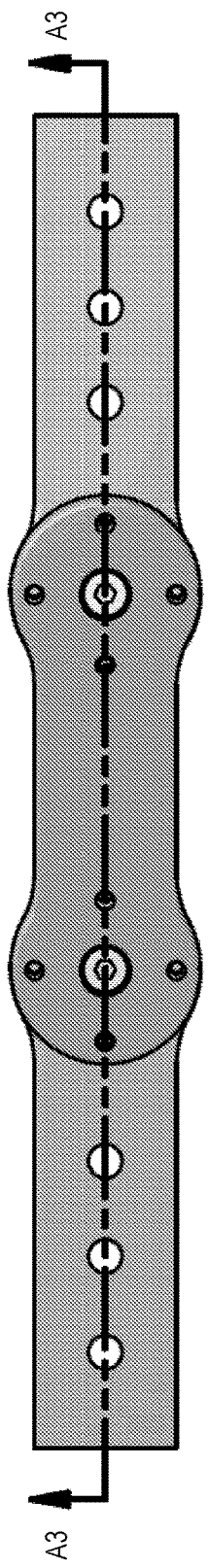
Figure 39:
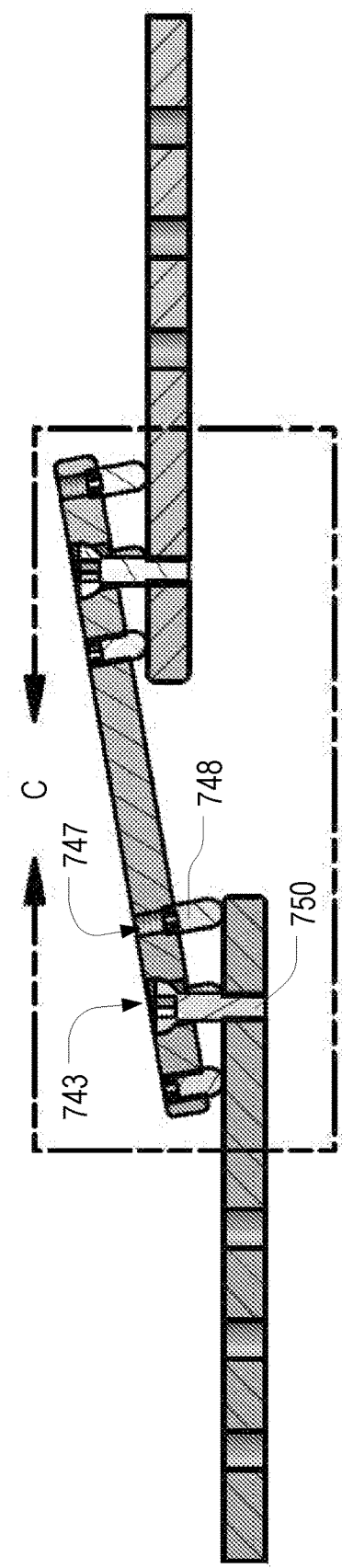
Figure 40:
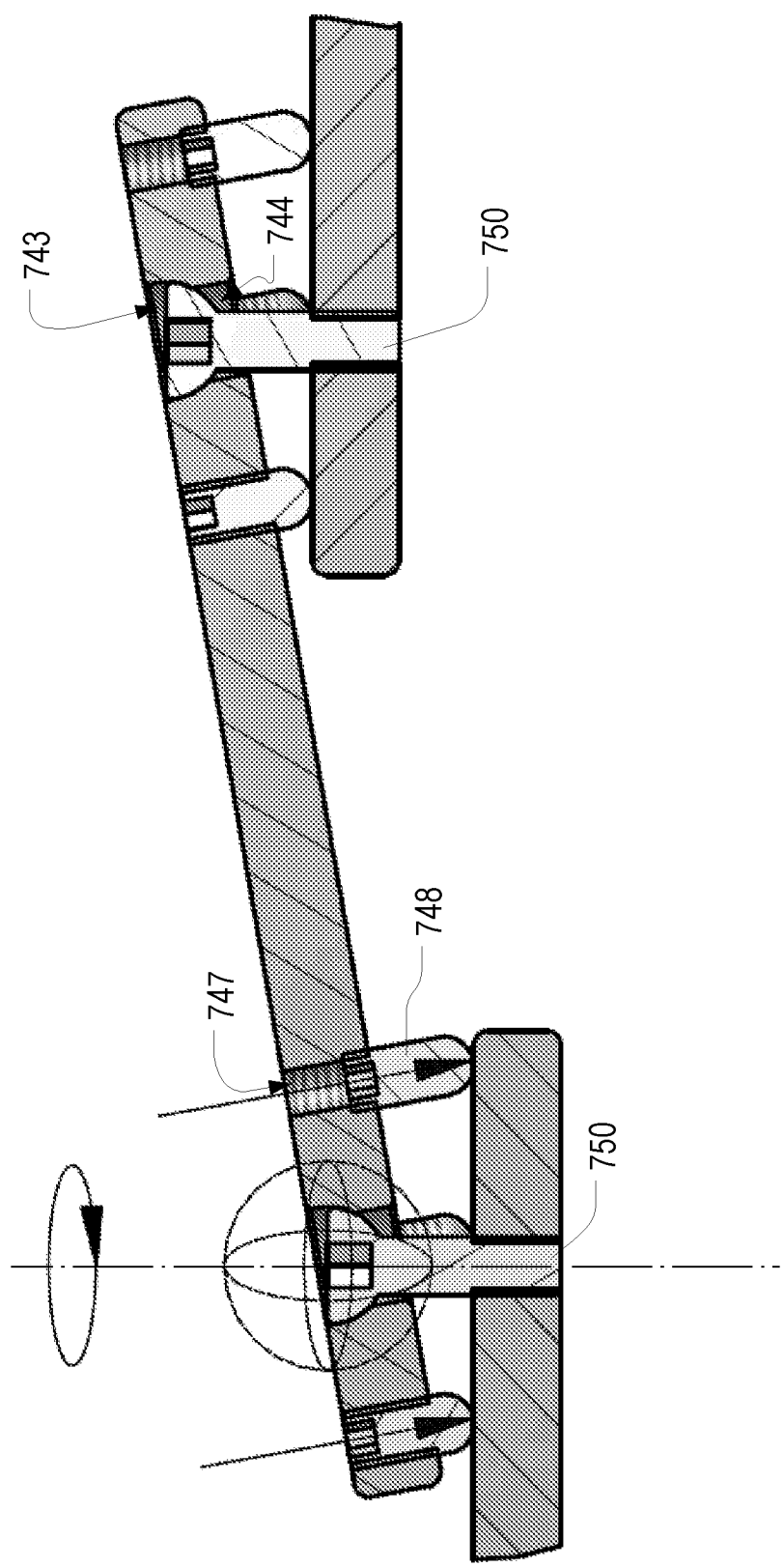

FIG. 36 illustrates another bone plate apparatus 710 in accordance with one or more preferred implementations. FIG. 37 is a side view of the bone plate apparatus 710, FIG. 38 is a top view of the bone plate apparatus 710, FIG. 39 is a cross-sectional view of the bone plate apparatus 610 along line A3 illustrated in FIG. 38, and FIG. 40 is a close-up cross-sectional view of the bone plate apparatus 710 showing the portion of the bone plate apparatus 710 within box C of FIG. 39.

The bone plate apparatus 710 includes a first plate 720, a second plate 730, and a linking segment 740. The first plate 720 includes a plurality of openings 724 defined therethrough for use in receiving bone screws for securement of the first plate 720 to bone, and the second plate 730 similarly includes a plurality of openings 734 defined therethrough for use in receiving bone screws for securement of the second plate 730 to bone.

The linking segment 440 includes, on each lengthwise side, four threaded adjustment passageways 747 defined therethrough having threaded adjustment pins 748 received therein (in accordance with one or more preferred implementations, adjustment screws or bolts may be utilized). The adjustment pins 748 can be rotated to increase or decrease an extent of the adjustment pin 748 extending out of the respective adjustment passageway 747 below a bottom of the linking segment 440.

The linking segment 740 further includes, on each lengthwise side, a central opening disposed between the threaded adjustment passageways 747. Each central opening provides access to a respective channel 743 having sloped walls that generally slope inward moving downward from a top side of the linking segment 740. Each channel 743 is open at a bottom thereof providing access to a respective channel passageway defined through the linking segment 740. Each channel 747 is shaped and dimensioned to accommodate and receive a head of a screw, with the inwardly sloping walls serving to prevent further passage of the head of the screw thus preventing a screw such as one of the screws 750 from traveling further within the corresponding channel passageway defined through the linking segment 740. Each plate 720,730 includes a threaded screw receiving channel configured to receive and engage a screw 750, as can be seen in FIG. 34. These screw receiving channels may be passageways defined through the entire plate, or may only be defined partially therethrough.

The bone plate apparatus 710 is configured such that, when a screw 750 is received within a channel 743 and the corresponding channel passageway and loosely screwed into the screw receiving channel of a plate, the screw 750 defines an axis for rotative movement of the linking segment 740 and plate relative to one another, as illustrated in FIG. 40. A screw 750 received within a channel 743 and corresponding channel passageway may be tightened to prevent such rotative movement.

Further, each channel 743 is configured to allow for three-dimensional orientation adjustments of the linking segment 440 relative to a plate even when a screw 750 is received within the channel 743, as illustrated in FIG. 40. In this regard, by manipulating the adjustment pins 748, a height and orientation of the linking segment 440 relative to a plate can be adjusted.

Exemplary Articulation Features

In accordance with one or more preferred implementations, a bone plate apparatus comprises an articulating joint disposed at a plate. In accordance with one or more preferred implementations, a bone plate apparatus comprises an articulating joint disposed at a linking segment. In accordance with one or more preferred implementations, a bone plate apparatus includes an articulating joint comprising one or more mechanisms disposed at a plate and one or more mechanisms disposed at a linking segment, the mechanisms being configured to be coupled or connected together to form the articulating joint.

In accordance with one or more preferred implementations, a linking segment comprises an articulating joint, with the articulating joint enabling adjustment of a first portion of the linking segment relative to a second portion of the linking segment. In accordance with one or more preferred implementations, a linking segment comprises two or more articulating joints, with each enabling adjustment of a portion of the linking segment relative to another portion of the linking segment.

In accordance with one or more preferred implementations, an articulating joint of a bone plate apparatus comprises mating curvatures, e.g. mating curved surfaces. In accordance with one or more preferred implementations, an articulating joint comprises mating curvatures, a bolt or screw, and an alignment washer. In accordance with one or more preferred implementations, an articulating joint comprises an alignment washer.

In accordance with one or more preferred implementations, an articulating joint of a bone plate apparatus comprises a ball and socket joint.

In accordance with one or more preferred implementations, an articulating joint of a bone plate apparatus comprises a multi-planar articulating joint.

In accordance with one or more preferred implementations, an articulating joint of a bone plate apparatus comprises a uniplanar joint.

In accordance with one or more preferred implementations, an articulating joint of a bone plate apparatus comprises a biaxial or universal joint.

In accordance with one or more preferred implementations, an articulating joint comprises two universal joints.

In accordance with one or more preferred implementations, an articulating joint of a bone plate apparatus is lockable to allow no deviation or motion.

In accordance with one or more preferred implementations, an articulating joint of a bone plate apparatus is semi-lockable to allow varying degrees of motion. In this regard, it is believed that treatment of fractures can be facilitated by allowing for a little bit of motion, and that healing can be facilitated by allowing bone ends to butt against one another (e.g. when walking).

In accordance with one or more preferred implementations, an articulating joint of a bone plate apparatus allows for restricted motion in specified planes (e.g. all of the time, when locked, or when semi-locked).

In accordance with one or more preferred implementations, an articulating joint may lock by screw, pin, weld, etc.

In accordance with one or more preferred implementations, a bone plate apparatus comprises a two or more different types of articulating joints.

In accordance with one or more preferred implementations, a mechanism providing an articulating joint may be removably couplable or connectable to a bone plate apparatus if needed.

In accordance with one or more preferred implementations, an articulating joint of a bone plate apparatus is configured to be translated or repositioned on or along a component of a bone plate apparatus (e.g. a ball and socket articulating joint could slide along the length of a plate).

In accordance with one or more preferred implementations, a bone plate apparatus may comprise a series of articulations.

In accordance with one or more preferred implementations, an articulating joint of a bone plate apparatus provides a range of motion sufficient to enable alignment of bone portions or boney segments in all planes of motion.

In accordance with one or more preferred implementations, an articulating joint of a bone plate apparatus provides a thirty degree range of motion.

In accordance with one or more preferred implementations, an articulating joint of a bone plate apparatus provides a forty five degree range of motion.

In accordance with one or more preferred implementations, an articulating joint of a bone plate apparatus is configured to lock via a bolt-in alignment washer system.

In accordance with one or more preferred implementations, an articulating joint of a bone plate apparatus is configured to lock via a set screw.

In accordance with one or more preferred implementations, an articulating joint of a bone plate apparatus is configured to lock via a lever and bar.

In accordance with one or more preferred implementations, an articulating joint of a bone plate apparatus is configured to lock via use of one or more textured surfaces.

In accordance with one or more preferred implementations, two plates may be configured to be connectable to each other, e.g. without a linking segment. In accordance with one or more preferred implementations, two plates are connected to each other at an articulating joint.

In accordance with one or more preferred implementations, a bone plate apparatus or a component thereof comprises two or more articulating joints.

Figure 41:
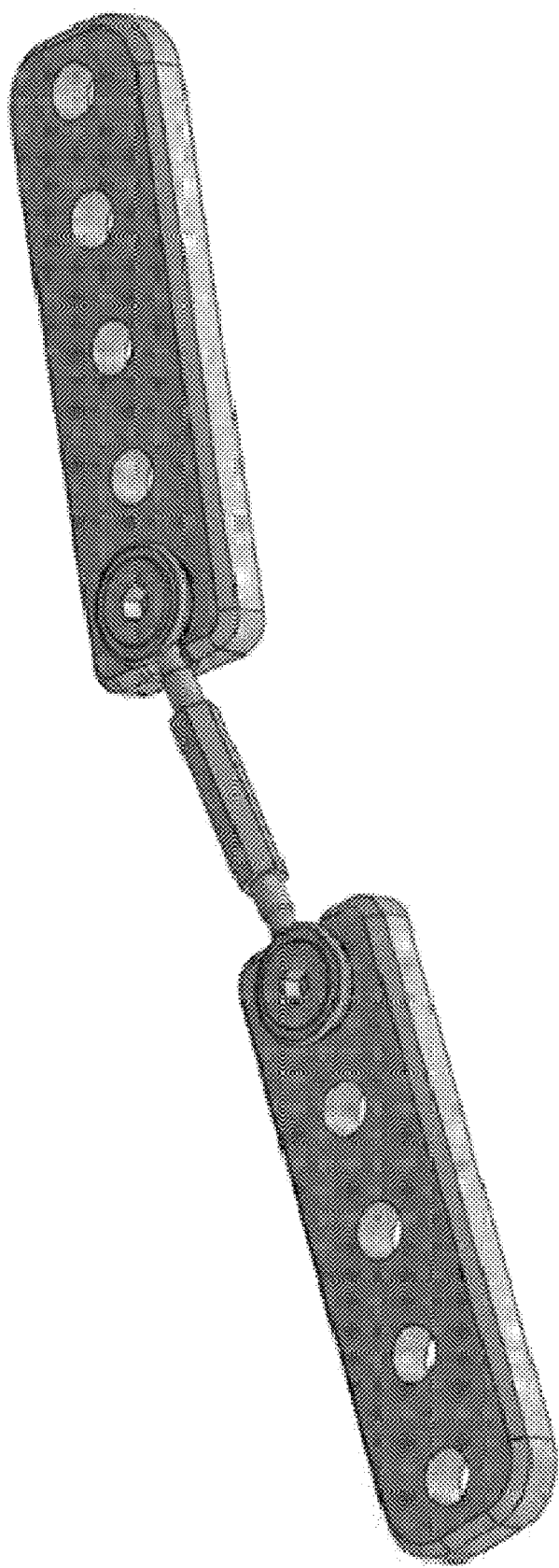
FIG. 41 illustrates features of an exemplary bone plate apparatus in accordance with one or more preferred implementations.

In accordance with one or more preferred implementations, a bone plate apparatus may comprise a first mechanism configured to provide for rotative adjustment, coupled with a second mechanism configured to provide for vertical adjustment, as illustrated in FIG. 41. In the implementation illustrated in FIG. 41, a cutout portion of a plate defines and limits a range of motion for the bone plate apparatus.

Exemplary Plate and Linking Segment Features

In accordance with one or more preferred implementations, a component of a bone plate apparatus (such as a plate or linking segment) has fixed dimensions (e.g. a fixed length).

In accordance with one or more preferred implementations, a component of a bone plate apparatus (such as a plate or linking segment) has one or more adjustable dimensions (e.g. an adjustable length).

In accordance with one or more preferred implementations, a component of a bone plate apparatus is rigid or semi-rigid.

In accordance with one or more preferred implementations, a component of a bone plate apparatus is radiolucent such that an x-ray can see through it (e.g. carbon).

In accordance with one or more preferred implementations, a component of a bone plate apparatus is compressible.

In accordance with one or more preferred implementations, a component of a bone plate apparatus is distressable.

In accordance with one or more preferred implementations, a component of a bone plate apparatus is distractable.

In accordance with one or more preferred implementations, a component of a bone plate apparatus is bendable or flexible.

In accordance with one or more preferred implementations, a component of a bone plate apparatus is absorbable.

In accordance with one or more preferred implementations, a component of a bone plate apparatus is dissolvable.

In accordance with one or more preferred implementations, a component of a bone plate apparatus is mechanized.

In accordance with one or more preferred implementations, a component of a bone plate apparatus is magnetic.

In accordance with one or more preferred implementations, a component of a bone plate apparatus includes one or more servo-motors.

In accordance with one or more preferred implementations, a component of a bone plate apparatus is flat.

In accordance with one or more preferred implementations, a component of a bone plate apparatus is round.

In accordance with one or more preferred implementations, a component of a bone plate apparatus has openings or holes for securement to a bone portion (e.g. screw holes). In accordance with one or more preferred implementations, a linking segment comprises such openings or holes, and may be configured or operable to function like a plate.

In accordance with one or more preferred implementations, a component of a bone plate apparatus comprises synthetic or biological material.

In accordance with one or more preferred implementations, a component of a bone plate apparatus comprises material which can stimulate or facilitate healing.

In accordance with one or more preferred implementations, a component of a bone plate apparatus is configured to contain and deliver a material or biological entity.

In accordance with one or more preferred implementations, a component of a bone plate apparatus is configured to deliver an electrical impulse.

In accordance with one or more preferred implementations, a component of a bone plate apparatus comprises a sensor. In accordance with one or more preferred implementations, a component of a bone plate apparatus comprises a strain gauge. A sensor or strain gauge may indicate how well a bone has healed, or communicate a signal that it is no longer feeling any pressure. A shock absorber may be utilized as, or in combination with, a sensor or strain gauge.

In accordance with one or more preferred implementations, a component of a bone plate apparatus comprises one or more radio or other communications components for communicating a wireless signal. In accordance with one or more preferred implementations, a radio or other communication component of a bone plate apparatus is configured to wirelessly communicate sensor data from a sensor of the bone plate apparatus.

In accordance with one or more preferred implementations, a component of a bone plate apparatus comprises electronic storage for storing sensor data.

In accordance with one or more preferred implementations, a component of a bone plate apparatus comprises a piezoelectric material. In accordance with one or more preferred implementations, a component of a bone plate apparatus comprises a piezoelectric sensor. In accordance with one or more preferred implementations, a component of a bone plate apparatus comprises a piezoelectric sensor which utilizes the piezoelectric effect to measure changes in strain or force by converting them to electric charge which is then measured by a sensor. In accordance with one or more preferred implementations, a component of a bone plate apparatus comprises an integrated circuit piezoelectric sensor. In accordance with one or more preferred implementations, a component of a bone plate apparatus comprises a piezoelectric accelerometer.

In accordance with one or more preferred implementations, a component of a bone plate apparatus comprises a flex sensor, a gyroscopic sensor, an impact sensor, an inclinometer, a position sensor, an angular rate sensor, a shock detector, a tilt sensor, a load cell, or a force gauge or sensor.

In accordance with one or more preferred implementations, a sensor is embedded in or secured to a plate or linking segment. In accordance with one or more preferred implementations, a segment of a plate or linking segment has sensor capabilities.

In accordance with one or more preferred implementations, a bone plate apparatus may comprise a plurality of linking segments.

In accordance with one or more preferred implementations, a bone plate apparatus may comprise a secondary support for strength (e.g. a secondary support adjacent to a linking segment).

In accordance with one or more preferred implementations, a plate of a bone plate apparatus is flat.

In accordance with one or more preferred implementations, a plate of a bone plate apparatus comprises a flat surface configured to engage a bone portion.

In accordance with one or more preferred implementations, a plate of a bone plate apparatus comprises a curved surface configured to engage a bone portion.

In accordance with one or more preferred implementations, a plate of a bone plate apparatus is oblong.

In accordance with one or more preferred implementations, a plate of a bone plate apparatus is around one inch long. In accordance with one or more preferred implementations, a plate of a bone plate apparatus is around one half of an inch long. In accordance with one or more preferred implementations, a plate of a bone plate apparatus is around one inch long. In accordance with one or more preferred implementations, a linking segment of a bone plate apparatus is around one inch long. In accordance with one or more preferred implementations, a linking segment of a bone plate apparatus is around one half of an inch long. In accordance with one or more preferred implementations, a plate of a bone plate apparatus is much longer than a linking segment of a bone plate apparatus. In accordance with one or more preferred implementations, a plate of a bone plate apparatus is much shorter than a linking segment of a bone plate apparatus.

In accordance with one or more preferred implementations, a bone plate apparatus is configured for use with, or incorporates, a cable. In accordance with one or more preferred implementations, a bone plate apparatus comprises one or more openings for passage of a cable therethrough which is wrapped around a bone portion. In accordance with one or more preferred implementations, a bone plate apparatus is secured to one or more bone portions by a cable. In accordance with one or more preferred implementations, a bone plate apparatus is secured to one or more bone portions at least partially by a cable.

In accordance with one or more preferred implementations, a bone plate apparatus comprises metal, plastics, ceramics, or other suitable materials.

In accordance with one or more preferred implementations, a bone plate apparatus comprises aluminum.

In accordance with one or more preferred implementations, a bone plate apparatus comprises steel.

Exemplary Additional Features

In accordance with one or more preferred implementations, a bone plate apparatus comprises one or more computer readable storage media. In accordance with one or more preferred implementations, a bone plate apparatus comprises flash storage. In accordance with one or more preferred implementations, a bone plate apparatus comprises a hard drive. In accordance with one or more preferred implementations, a bone plate apparatus comprises a solid state drive.

In accordance with one or more preferred implementations, captured sensor data is stored at computer readable storage media at the bone plate apparatus for later access. In accordance with one or more preferred implementations, a bone plate apparatus comprises wireless communication components (e.g. a transmitter and receiver or transceiver) for wireless communication of captured or stored sensor data. In accordance with one or more preferred implementations, a bone plate apparatus is configured for Bluetooth or Wi-Fi. In accordance with one or more preferred implementations, a bone plate apparatus comprises an interface port for electronic communication of captured or stored sensor data.

In accordance with one or more preferred implementations, a bone plate apparatus comprises a battery, and includes one or more battery powered sensors. In accordance with one or more preferred implementations, a bone plate apparatus comprises a rechargeable battery, and one or more ports for connecting a cord for recharging of the rechargeable battery. In accordance with one or more preferred implementations, a bone plate apparatus comprises a removable rechargeable battery.

In accordance with one or more preferred implementations, an articulating joint of a bone plate apparatus comprises a multi-directional joint that is liquid rather than mechanical. In accordance with one or more preferred implementations, such a liquid joint comprises or consists of a bi-phasic material interface.

Exemplary Use Methodologies

In accordance with one or more preferred implementations, a bone plate apparatus comprising two plates and one or more articulating joints is used in a methodology where the plates are attached to bone portions on either side of a fracture with at least one of the one or more articulating joints unlocked, the bone portions are aligned, and then any unlocked articulating joints are locked, establishing a fixed alignment of the plates. Subsequently, if needed, one or more of the articulations can be unlocked, the bone portions realigned, and the articulations then relocked.

In accordance with one or more preferred implementations, a linking segment is attached or connected to a plate prior to securement of the plate to a bone portion. In accordance with one or more preferred implementations, a linking segment is attached or connected to a plate that is already secured to a bone portion.

In accordance with one or more preferred implementations, a kit is provided which includes linking segments of various lengths, and a linking segment having an appropriate length is selected for use and connected to one or more plates, either before or after they have been secured to a bone portion.

In accordance with one or more preferred implementations, a first plate is secured to a bone portion, then a linking segment is connected to the first plate, then the linking segment is connected to a second plate, and then the second plate is secured to a bone portion.

In accordance with one or more preferred implementations, a first plate is secured to a bone portion, then a linking segment is connected to the first plate, then a second plate is secured to a bone portion, and then the linking segment is connected to the second plate.

In accordance with one or more preferred implementations, a linking segment is connected to a first plate, then the first plate is secured to a bone portion, then the linking segment is connected to a second plate, and then the second plate is secured to a bone portion.

In accordance with one or more preferred implementations, a linking segment is connected to a first plate, then the first plate is secured to a bone portion, then a second plate is secured to a bone portion, and then the linking segment is connected to the second plate.

In accordance with one or more preferred implementations, a first plate is connected to a second plate, then the first plate is secured to a bone portion, and then the second plate is secured to a bone portion.

In accordance with one or more preferred implementations, a first plate is secured to a bone portion, then the first plate is connected to a second plate, and then the second plate is secured to a bone portion.

In accordance with one or more preferred implementations, a first plate is secured to a bone portion, then a second plate is secured to a bone portion, and then the first plate is connected to the second plate.

In accordance with one or more preferred implementations, a configuration of a bone plate apparatus is pre-set based upon radiologic studies (e.g. the relative position of first and second plates relative to a linking segment and a length of the linking segment is pre-set based on x-ray information).

In accordance with one or more preferred implementations, a bone plate apparatus is utilized to control a broken bone in two or more fragments.

In accordance with one or more preferred implementations, a bone plate apparatus is utilized to span boney deformities.

In accordance with one or more preferred implementations, a bone plate apparatus is utilized to correct deformities.

In accordance with one or more preferred implementations, a bone plate apparatus is utilized in an osteotomy context.

In accordance with one or more preferred implementations, a bone plate apparatus is utilized for limb lengthening and deformity correction.

In accordance with one or more preferred implementations, a bone plate apparatus is utilized in a veterinary context.

In accordance with one or more preferred implementations, a bone plate apparatus is utilized to facilitate correction of a crooked bone.

In accordance with one or more preferred implementations, a bone plate apparatus is utilized in treatment of a crooked bone.

In accordance with one or more preferred implementations, a bone plate apparatus is utilized in an osteonomy context.

In accordance with one or more preferred implementations, two plates of a bone plate apparatus are secured to a bone, the bone is cut, then the bone plate apparatus is adjusted to a desired position, and then a configuration of the bone plate apparatus is locked.

In accordance with one or more preferred implementations, a bone plate apparatus is secured to bone portions and locked in a particular configuration or orientation, an x-ray is taken, and then one or more articulating joints of the bone plate apparatus are unlocked and further adjustment of the configuration or orientation of the bone plate apparatus occurs, and then the articulating joint is relocked. In accordance with one or more preferred implementations, this further may include unlocking and adjustment of an extendible or length-adjustable linking mechanism. In accordance with one or more preferred implementations, this may include adjustment of a position of an articulating joint mechanism. In accordance with one or more preferred implementations, such a process may be repeated with additional x-ray imaging followed by additional adjustment, etc.

In accordance with one or more preferred implementations, three dimensional computer modeling is utilized to determine a proper configuration or orientation for a bone plate apparatus relative to one or more bones of a patient. In accordance with one or more preferred implementations, a user of a three dimensional computer modeling program is able to manipulate a model of a bone plate apparatus relative to a model of one or more bones of a patient to determine a preferred configuration or orientation. In accordance with one or more preferred implementations, a three dimensional computer modeling program is configured to automatically calculate a preferred configuration or orientation.

In accordance with one or more preferred implementations, data or information regarding orientation of a first bone of a patient is utilized to determine a desired configuration or orientation for portions of a bone or plates of a bone plate apparatus. For example, data regarding a first leg of a patient may be utilized to determine a preferred orientation for bone portions of the second leg of the patient, and may be utilized to determine a preferred configuration or orientation for a bone plate apparatus. In accordance with one or more preferred implementations, three dimensional computer modeling is utilized to facilitate determination of a preferred orientation for bone portions or a preferred configuration or orientation for a bone plate apparatus.

In accordance with one or more preferred implementations, a computer program is configured to robotically manipulate a bone plate apparatus to position it in a desired configuration or orientation. In accordance with one or more preferred implementations, a computer program is configured to generate three dimensional printing data to 3D print a bone plate apparatus in a desired configuration or orientation, or a model of a bone plate apparatus in a desired configuration or orientation. In accordance with one or more preferred implementations, a computer program is configured to generate three dimensional printing data to 3D print a plate having a bone-specific curvature for a bone plate apparatus.

In accordance with one or more preferred implementations, alignment wires can be used with a bone plate apparatus. For example, alignment wires can be screwed into a plate, x-ray imaging can be done, and the x-ray image can then be used to facilitate orientation of bone portions or orientation or configuration of the bone plate apparatus.

In accordance with one or more preferred implementations, x-ray imaging of a bone plate apparatus, such as a bone plate apparatus with alignment wires, may be used to follow or track loss or reduction of compression.

In accordance with one or more preferred implementations, a bone plate apparatus may be utilized in a manner such that, following loss or reduction of compression, further adjustment of the bone plate apparatus may be performed to mitigate or alleviate such loss or reduction of compression.

In accordance with one or more preferred implementations, a bone plate apparatus may have alignment markers or indicators built into it or marked thereon. In accordance with one or more preferred implementations, an articulating joint of a bone plate apparatus includes alignment markers or indicators. In accordance with one or more preferred implementations, a bone plate apparatus may have alignment markers built therein configured to allow orientation of components of the bone plate apparatus to be determined via x-ray imaging. For example, in accordance with one or more preferred implementations, a bone plate apparatus enables a methodology involving taking one or more x-ray images of an installed bone plate apparatus, and determining therefrom a degree of rotation of a first component of the bone plate apparatus relative to a second component of the bone plate apparatus.

In accordance with one or more preferred implementations, an articulating joint of a bone plate apparatus is configured for analog movement through a fixed number of possible positions, e.g. manipulation of an articulating joint to rotate it two "clicks" in a ratchet-like manner. In accordance with one or more preferred implementations, each possible position may represent a difference of a fixed number of degrees from a prior position, e.g. a difference of one degree or a difference of three degrees.

In accordance with one or more preferred implementations, a bone plate apparatus comprises one or more removably attachable joy sticks which can be removably attached to a plate or linking segment to facilitate manipulation of the bone plate apparatus. In accordance with one or more preferred implementations, a removably attachable joystick can be screwed into a threaded channel of a bone plate apparatus. In an exemplary preferred methodology, clamps are utilized to engage one or more joysticks of a bone plate, and used to align, configure, or orient a bone plate apparatus.

In accordance with one or more preferred implementations, clamps are used to align, configure, or orient a bone plate apparatus.

In accordance with one or more preferred implementations, one or more components of a bone plate apparatus are configured to have a clamp hook into the bone plate apparatus (e.g. hook into a plate or linking segment of a bone plate apparatus).

In accordance with one or more preferred implementations, a bone plate apparatus is configured to include an articulating joint mechanism the location of which can be adjusted on a plate and/or linking mechanism. For example, a plate may include an articulating joint mechanism which can slide or translate along a plate (e.g. along a length of a plate).

In accordance with one or more preferred implementations, features and methodologies disclosed herein are utilized in the context of an intermedullary rod. In accordance with one or more preferred implementations, an intermedullary rod comprises one or more articulating joints.

In accordance with one or more preferred implementations, a bone plate apparatus comprising a universal joint connecting two plates is utilized to facilitate correction of rotation of two bone portions relative to one another.

In accordance with one or more preferred implementations, an articulating joint of a bone plate apparatus is adjustable percutaneously following installation and securement to bone portions, e.g. via a methodology involving an incision, unlocking the articulating joint, repositioning or reconfiguring the bone plate apparatus, and then relocking the articulating joint.

In accordance with one or more preferred implementations, an articulating joint of a bone plate apparatus is adjustable percutaneously following installation and securement to bone portions, e.g. via a methodology involving an incision, unlocking the articulating joint, setting bone portions by repositioning or reconfiguring the bone plate apparatus, and then relocking the articulating joint.

In accordance with one or more preferred implementations, an articulating joint of a bone plate apparatus is adjustable percutaneously following installation and securement to bone portions, e.g. via a methodology involving an incision, unlocking the articulating joint, repositioning or reconfiguring the bone plate apparatus by setting bone portions, and then relocking the articulating joint.

In accordance with one or more preferred implementations, an articulating joint of a bone plate apparatus is adjustable percutaneously following installation and securement to bone portions, e.g. via a methodology involving an incision, unlocking the articulating joint, setting bone portions, and then relocking the articulating joint.

Innovative Linking Segment Functionality

As noted above, adjustable bone plates are known, including adjustable bone plates with joints providing a connection between plate members.

However, bone plate apparatus in accordance with one or more preferred implementations are believed to facilitate or enable innovative functionality over and above known adjustable bone plates via innovative structural configuration, and innovative methodologies enabled thereby.

As an example, a structural configuration involving use of a linking segment and two multiplanar articulating joints each connecting the linking segment to a respective plate is believed to be innovative and provide innovative functionality over known bone plates.

As another example, a structural configuration involving use of a removably connectable linking segment is believed to enable installation methodologies not possible with known bone plates.

As yet another example, a structural configuration involving a linking segment and two multiplanar articulating joints each connecting the linking segment to a respective plate, where the configuration allows for adjustment of a length or extent of the linking segment extending between the two plates, is believed to be innovative and provide innovative functionality over known bone plates.

In accordance with one or more preferred implementations, a bone plate apparatus comprises first and second plates, a linking segment comprising a rod, and first and second ball and socket joints each connecting a respective one of the plates to the linking segment. In accordance with one or more preferred implementations, the rod of the linking segment is configured to slide through one or both of the ball and socket joints to enable adjustability of an extent of the linking segment extending between the two plates.

Based on the foregoing description, it will be readily understood by those persons skilled in the art that the present invention has broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:
1. A method comprising:
(a) attaching a first plate to bone at a first bone location;
(b) connecting a linking segment having an adjustable length to the first plate such that the two are connected at a first articulating joint that enables movement simultaneously through two perpendicular planes with a limited range of motion;

(c) connecting the linking segment to a second plate such that the two are connected at a second articulating joint that enables movement simultaneously through two perpendicular planes with a limited range of motion;

(d) orienting the first plate relative to the second plate by effecting adjustment at one of the articulating joints;

(e) attaching the second plate to bone at a second bone location;

(f) locking the first and second articulating joints; and (g) locking adjustability of a length of the linking segment;

(h) wherein the first plate and the second plate are interconnected only by the linking segment being connected to the first plate and the second plate.

2. The method of claim 1, wherein the method further comprises unlocking one or more of the articulating joints; orienting the first plate relative to the second plate by effecting adjustment at one of the articulating joints; and locking the first and second articulating joints.

3. The method of claim 1, wherein the method further comprises unlocking one or more of the articulating joints; orienting, based on x-ray imaging information, the first plate relative to the second plate by effecting adjustment at one of the articulating joints; and locking the first and second articulating joints.

4. The method of claim 1, wherein the first plate comprises a flat surface configured to engage a bone portion.

5. The method of claim 1, wherein the first plate comprises a curved surface configured to engage a bone portion.

6. The method of claim 1, wherein bone screws are used to attach the first bone plate to the first bone location.

7. The method of claim 6, wherein bone screws are used to attach the second bone plate to the second bone location.

8. The method of claim 1, wherein bone screws are used to attach the second bone plate to the second bone location.

9. The method of claim 1, wherein the first articulating joint is a ball and socket joint with range of motion limited by a shape of the socket.

10. The method of claim 9, wherein the second articulating joint is a ball and socket joint with range of motion limited by a shape of the socket.

11. The method of claim 1, wherein the second articulating joint is a ball and socket joint with range of motion limited by a shape of the socket.

12. The method of claim 1, wherein the method further comprises unlocking one or more of the articulating joints; orienting the first plate relative to the second plate by effecting adjustment at one of the articulating joints; and locking the first and second articulating joints.

13. The method of claim 1, wherein the method further comprises unlocking one or more of the articulating joints; orienting, based on x-ray imaging information, the first plate relative to the second plate by effecting adjustment at one of the articulating joints; and locking the first and second articulating joints.

14. A method comprising:

(a) attaching a first plate to bone at a first bone location;

(b) connecting a linking segment having an adjustable length to the first plate such that the two are connected at a first articulating joint;

(c) connecting the linking segment to a second plate such that the two are connected at a second articulating joint;

(d) orienting the first plate relative to the second plate by effecting adjustment at one of the articulating joints;

(e) attaching the second plate to bone at a second bone location;

(f) locking the first and second articulating joints; and (g) locking adjustability of the length of the linking segment;

(h) wherein the first plate and the second plate are interconnected only by the linking segment being connected to the first plate and the second plate; and (i) wherein each of the first articulating joint and the second articulating joint is a ball and socket joint.

15. The method of claim 14, wherein a range of motion of each of the first articulating joint and the second articulating joint is limited by a shape of the socket.

16. The method of claim 14, wherein the first plate comprises a flat surface configured to engage a bone portion.

17. The method of claim 14, wherein the first plate comprises a curved surface configured to engage a bone portion.

18. The method of claim 14, wherein bone screws are used to attach the first bone plate to the first bone location.

19. The method of claim 18, wherein bone screws are used to attach the second bone plate to the second bone location.

20. The method of claim 14, wherein bone screws are used to attach the second bone plate to the second bone location.

* * * * *